(12) United States Patent
Lin

(10) Patent No.: US 8,044,033 B2
(45) Date of Patent: Oct. 25, 2011

(54) FLUOROCYTIDINE DERIVATIVES AND COX-2 INHIBITORS FOR THE TREATMENT OF CANCER

(75) Inventor: Edward H. Lin, Bellevue, WA (US)

(73) Assignee: The Board of Regents of the University of Texas System, Austin, TX (US)

( * ) Notice: Subject to any disclaimer, the term of this patent is extended or adjusted under 35 U.S.C. 154(b) by 253 days.

(21) Appl. No.: 12/281,160

(22) PCT Filed: Mar. 2, 2007

(86) PCT No.: PCT/US2007/063236
§ 371 (c)(1),
(2), (4) Date: Nov. 20, 2008

(87) PCT Pub. No.: WO2007/103828
PCT Pub. Date: Sep. 13, 2007

(65) Prior Publication Data
US 2009/0156548 A1 Jun. 18, 2009

Related U.S. Application Data

(60) Provisional application No. 60/779,146, filed on Mar. 2, 2006.

(51) Int. Cl.
*A01N 43/04* (2006.01)
*A61K 31/70* (2006.01)
(52) U.S. Cl. ........... 514/49; 514/23; 514/42; 514/43
(58) Field of Classification Search .......... None
See application file for complete search history.

(56) References Cited

U.S. PATENT DOCUMENTS

| | | | |
|---|---|---|---|
| 6,537,988 B2 | 3/2003 | Lee | 514/221 |
| 2005/0227929 A1 | 10/2005 | Masferrer | 514/27 |

OTHER PUBLICATIONS

Khamly et al. Expert Opin. Investig. Drugs (2005), vol. 14, pp. 607-628.*
Ben-Josef et al. Journal of Clinical Oncology (2005), vol. 23, pp. 8739-8747.*
Ayanian et al. Journal of Clinical Oncology (2003), vol. 21, pp. 1293-1300.*
Koehne et al. Seminars in Oncology (2004), vol. 31, pp. 12-21.*
Abushullaih et al., "Incidence and severity of hand-foot syndrome in colorectal cancer patients treated with capecitabine: a single-institution experience," *Cancer Invest.*, 20:3-10, 2002.
Blanquicett et al., "Antitumor efficacy of capecitabine and celecoxib in irradiated and lead-shielded, contralateral human BxPC-3 pancreatic cancer xenografts: clinical implications of abscopal effects," *Clin. Cancer Res.*, 11:8773-8781, 2005.
Chu, "Efficacy and safety of capacitabine therapy for colorectal cancer," *Amer. J. of Oncology Review*, 2(5), Suppl. 3:1-28, 2003.

Cianchi et al., "Up-regulation of cyclooxygenase 2 gene expression correlates with tumor angiogenesis in human colorectal cancer," *Gastroenterology*, 121:1339-1347, 2001.
Demetri et al., "Phase 3, multicenter, randomized, double-blind, placebo-controlled trial of SU11248 in patients (pts) following failure of imatinib for metastatic GIST," *Proc. Am. Soc. Clin. Oncol.*, 23:308, 2005.
Diaz Rubio et al., "Cetuximab in combination with oxaliplatin/5-fluorouracil (5-FU)/folinic acid (FA) (FOLFOX-4) in the first-line treatment of patients with epidermal growth factor receptor (EGFR)-expressing metastatic colorectal cancer: An international phase II study," *Proc. Am. Soc. Clin. Oncol.*, 23(16s):3535, 2005.
El-Rayes et al., "A Phase II Trial of Celecoxib, Irinotecan, and Capecitabine in Metastatic Colorectal Cancer," *Proc. Am. Soc. Clin. Oncol.*, 23(308):3677, 2005.
Escudier et al., "Randomized Phase III trial of the Raf kinase and VEGFR inhibitor sorafenib (BAY 43-9006) in patients with advanced renal cell carcinoma (RCC)," *Proc. Am. Soc. Clin. Oncol.*, 23(308):4510, 2005.
Fürstenberger et al., "Circulating endothelial cells and angiogenic serum factors during neoadjuvant chemotherapy of primary breast cancer," *Br. J. Cancer*, 94(4):524-531, 2006.
Grothey et al., "Survival of patients with advanced colorectal cancer improves with the availability of fluorouracil-leucovorin, irinotecan, and oxaliplatin in the course of treatment," *J. Clin. Oncol.*, 22:1209-1214, 2004.
Hochster, "Bevacizumab in combination with chemotherapy: first-line treatment of patients with metastatic colorectal cancer," *Semin. Oncol.*, 33:S8-14, 2006.
International Search Report and Written Opinion issued in International Application No. PCT/US07/63236, mailed Sep. 25, 2007.
Jemal et al., "Cancer statistics, 2005," *CA Cancer J. Clin.*, 55:10-30, 2005.
Kerbel and Kamen, "The anti-angiogenic basis of metronomic chemotherapy," *Nat. Rev. Cancer*, 6:423-436, 2004.
Lin et al., "A phase II study of capecitabine and concomitant boost radiotherapy (XRT) in patients (pts) with locally advanced rectal cancer (LARC)," *Proc. Am. Soc. Clin. Oncol.*, 23:269, 2005.
Lin et al., "Retrospective study of capecitabine and celecoxib in metastatic colorectal cancer: potential benefits and COX-2 as the common mediator in pain, toxicities and survival?," *Am. J. Clin. Oncol.*, 29(3):232-239, 2006.
Masferrer et al., "Antiangiogenic and antitumor activities of cyclooxygenase-2 inhibitors," *Cancer Res.*, 60:1306-1311, 2000.
Solomon et al., "Cardiovascular risk associated with celecoxib in a clinical trial for colorectal adenoma prevention," *N. Engl. J. Med.*, 352:1071-1080, 2005.

* cited by examiner

*Primary Examiner* — Patrick Lewis
(74) *Attorney, Agent, or Firm* — Fulbright & Jaworski L.L.P.

(57) ABSTRACT

The present invention provides, in certain embodiments, methods for the treatment of colorectal cancer comprising administering a COX-2 inhibitor and fluorocytidine derivative to a human patient. In certain embodiments, a radiation therapy is also administered to the patient.

20 Claims, 10 Drawing Sheets

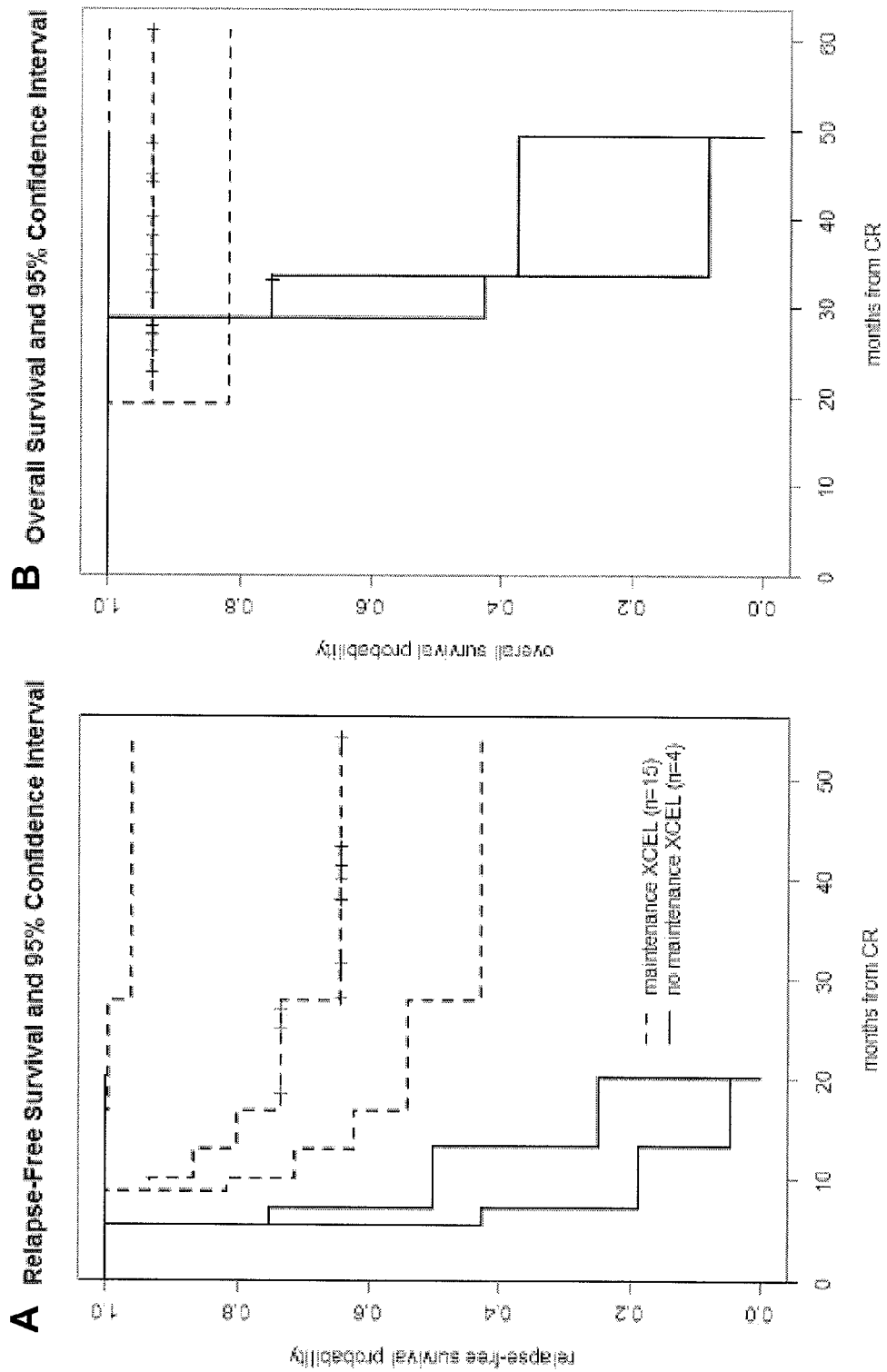
FIG. 10A-B

FLUOROCYTIDINE DERIVATIVES AND COX-2 INHIBITORS FOR THE TREATMENT OF CANCER

This application is a national phase application under 35 U.S.C. §371 of International Application No. PCT/US2007/063236 filed Mar. 2, 2007, which claims the benefit of U.S. Provisional Patent Application No. 60/779,146, filed on Mar. 2, 2006.

BACKGROUND OF THE INVENTION

1. Field of the Invention

The present invention relates generally to the fields of cancer therapy.

2. Description of Related Art

Colorectal cancer is the second most common cause of cancer-related death in the United States (Jemal et al., 2005). The benchmark median overall survival of patients receiving first-line and second-line combination chemotherapy for metastatic colorectal cancer is currently 17-20 months and 10-12 months, respectively (Douillard et al., 2000; Goldberg et al., 2004; Tournigand et al., 2004; Rothenberg et al., 2003; Hurwitz et al., 2004; Giantonio et al., 2005; Cunningham et al., 2004; Diaz Rubio et al., 2005). Unfortunately, the five year overall survival was merely 5-8%.

Various combination therapies have been used to address this form of cancer. Combining bevacizumab or cetuximab with cytotoxic chemotherapy produced response rate to 60-80%, converting more patients to be surgically resectable, but not overall CR rate ranging between 2-10% (Hurwitz et al., 2004; Diaz Rubio et al., 2005; Hochster, 2006). However, little is known about natural history of the 2-10% CR patients from chemotherapy, as majority do relapse within two years. The natural history of these surgical CR patients may be the closest approximation to that of the CR patients rendered by chemotherapy. Even though metastatic colorectal cancer is a systemic disease, selecting patients with liver only metastasis to undergo surgical resection leads to a five-year survival rate of 30-40% (Fong, 2000; Topham and Adam, 2002). In reality, only 2,300 (4%) of 60,000 patients with recurrent colorectal cancer per year may be "cured" with surgery among the 6,800 (11%) resectable patients. Five year overall survival rate for patients who had R0 (margin free) resection of metastasis was 40% compared to 0% for those with R1/R2 (close or gross margin resection or with radiofrequency ablation alone) (Abdalla et al., 2004). Adam et al reported a five-year overall survival of 34% for patients with unresectable liver metastatasis who then achieved surgical resection after response with chemotherapy (Adam et al., 2001). Adjuvant hepatic directed therapy in patients with resected liver metastasis remained controversial and appeared to impact only two-year hepatic recurrence free survival (Kemeny et al., 1999). Not surprisingly, the five year survival for patient with best tumor characteristics (solitary tumor <5 cm; disease free interval >12 months; CEA<200; node negative primary tumor) approached 60% (Fong et al., 1999). Intensive neoadjuvant and adjuvant chemotherapy in 47 patients with resectable liver metastasis produced response rate of 77% and median progression free survival of 21 months, and five year survival of 60% (Taieb et al., 2005). Much improvement for survival are needed for those with resectable liver metastasis and more so for those with unresectable metastases.

Some further combination chemotherapy often consists of 5-fluorouracil (5-FU), administered via infusional pumps and either irinotecan or oxaliplatin with bevacizumab or cetuximab (Hurwitz et al., 2004; Giantonio et al., 2005; Cunningham et al., 2004; Diaz Rubio et al., 2005). These treatments require placement of indwelling catheters and infusion pumps and produce a broad spectrum of serious toxicities, including myelosuppresion, diarrhea, neuropathy, skin rash, hypertension and rare bowel perforations (Douillard et al., 2000; Goldberg et al., 2004; Tournigand et al., 2004; Rothenberg et al., 2003; Hurwitz et al., 2004; Giantonio et al., 2005; Cunningham et al., 2004; Diaz Rubio et al., 2005). An equally effective, less toxic treatment that can be orally administered would be most appealing to patients (Borner et al., 2002). Capecitabine (XELODA®; Roche Pharmaceuticals, Nutley, N.J.) is an oral fluoropyrimidine pro-drug that is preferentially activated to 5-FU in tumor tissue. First-line treatment of metastatic colorectal cancer with capecitabine produced 25% response rates and improved toxicity profiles without overall survival benefits (12 months) compared with bolus 5-FU (Van Cutsem et al., 2001; Hoff et al., 2001) .Therefore, capecitabine is often combined with intravenously injected agents such as oxaliplatin or irinotecan for improved survival, so advantage of oral convenience is not fully exploited (Patt et al., 2004; Cassidy et al., 2004).

Like protracted 5-FU infusion, capecitabine at 1250 mg/m$_2$/day bid for two weeks every 3 weeks was also associated with increased incidence of hand-foot syndrome (HFS) occurring in 54% of the patients with 18% being grade 3 (Van Cutsem et al., 2001; Hoff et al., 2001; Meta-Analysis Group In Cancer, 1998). HFS is characterized by painful, erythematous swelling of the hands and feet that progresses to blisters within the first few weeks of starting therapy (Abushullaih et al., 2002). HFS is not life threatening, but may significantly interfere with daily activities and frequently reoccurs even after the second or third dose reductions (Abushullaih et al., 2002). There are no proven measures for HFS except for dose schedule modification and topical emollient (Nagore et al., 2000). Claims that high dose pyridoxine could prevent HFS have not been substantiated (Fabian et al., 1990). Because HFS possesses erythema, swelling, heat and pain, we postulated that HFS is an inflammatory process as a result of cyclooxygenase-2 (COX-2) activation, which is also prognostic marker for colorectal cancer progression and survival (Lin et al., 2002; Howe and Dannenberg, 2002; Sheehan et al., 1999). In xenograft models, adding celecoxib (XCEL) (CELEBREX®; Pfizer, New York, N.Y.) a selective COX-2 inhibitor, to chemotherapy or radiation therapy significantly increased antitumor efficacy compared to either treatment modality alone (Cianchi et al., 2001; Masferrer et al., 2000; Sheng et al., 1998; Milas, 2003). The preliminary findings suggested reduced HFS and improved survival for those with metastatic colorectal cancer who took XCEL (n=32) versus those who took capecitabine alone (n=35); however, more patients in the XCEL group receiving chemo-radiation (Lin et al., 2002). Given the survival benefits and unexpected response including complete responses, we expanded the study cohort (including the initial 32 patients who had XCEL) and performed analysis on the time course of HFS, response rate and survival stratified according to their prior chemotherapy or radiation.

The inventors reported in a retrospective study of 66 patients with metastatic colorectal cancer who underwent XCEL+/−radiation therapy experienced reduced toxicities notably hand-foot syndrome and improved overall survival in both first-line and second-line setting. Given that nineteen (29%) of sixty-six patients unexpectedly achieved CR with XCEL alone (n=9) or with radiation (n=12) including six were surgical CR after response, the inventors undertook a detailed analysis of tumor characteristics, pattern and duration of CR and relapse in relationship to diagnosis of cancer, first-line therapy, XCEL and surgery.

SUMMARY OF THE INVENTION

In a first embodiment, the invention provides improved methods for the treatment of cancer in a patient comprising administering to the patient an effective amount of a fluorocytidine derivative and a COX-2 enzyme inhibitor. As used in this embodiment a an "effective amount" may comprise an effective amount of to reduce or inhibit cancer metastasis, metastasis growth or over-all probability of cancer relapse. In some aspects, the COX-2 selective enzyme inhibitor may be meloxicam, valdecoxib (BEXTRA®), celecoxib (CELEBREX®), rofecoxib (VIOXX®) or naproxen (ALEVE®). While in a preferred embodiment the COX-2 inhibitor for use in the instant methods is celecoxib, it is contemplated that a COX-2 inhibitor other than celecoxib is included as part of the invention. Furthermore, in preferred embodiments, a fluorocytidine derivative derivative is a 5'-deoxy-5-fluorocytidine derivative or a derivative described in U.S. Pat. No. 4,966,891 incorporated herein by reference. Thus, while in a preferred embodiment a fluorocytidine derivative for use in methods of the invention is capecitabine inhibitors other than capecitabine are considered with-in the scope of the current invention.

Thus, in some very specific embodiments, there is provided a method for treating a patient with cancer comprising administering celecoxib and capecitabine to a human patient. Thus in certain aspects there is provided a method for treating cancer in a patient, such as a human patient, comprising administering capecitabine and celecoxib to the patient. In some aspects, methods of the invention may be further defined as a method for reducing the probability of capecitabine-induced hand-foot syndrome (HFS) in the patient. In still further aspects of the invention there is provided a method for reducing the severity of HFS in a patient receiving or who has received capecitabine administration comprising administering to the patient an effective amount of a COX-2 specific inhibitor (i.e., celecoxib).

A variety of cancers may be treated by methods of the invention. For example, a cancer for treatment may originate in the bladder, blood, bone, bone marrow, brain, colon, esophagus, gastrointestine, head, kidney, liver, lung, nasopharynx, neck, pancreas, prostate, skin, stomach, testis, tongue, or uterus. Thus, in some preferred aspects, the cancer may be a gastrointestinal cancer or a colorectal cancer. Furthermore, in certain aspects, a cancer may be defined as metastatic cancer such as a metastatic colorectal cancer. Various types of metastases may be treated including but, not limited to, a nodal metastasis, a solitary nodal metastasis, a clustered nodal metastasis, a visceral metastasis, a peritoneal metastasis, or a hepatic or extrahepatic metastasis. Thus, in certain aspects, the invention provide a method for inhibiting the growth or development of micro metastases. Of course methods for treating an unmetastasized cancer are also included as part of the invention.

As used herein the term "patient" is typically used to refer to a human patient but may also comprise non-human animals. In certain cases, the treated patient has not been previously treated for the cancer. However, in other cases, the patient has been previously treated for the cancer. For instance, the patient may have been treated by administration of a chemotherapeutic such as irinotecan or by administration of a surgical procedure, radiation or an immunotherapeutic. Furthermore, the patient may have undergone treatment for a cancer that is the same or different than the type of cancer to be treated by methods of the invention.

In yet further aspects, methods of the invention may be used in combination with or in conjunction with additional anti-cancer therapies. For example, a second cancer therapy for use in the invention may be administration of a chemotherapeutic, an anti-cancer drug, a surgical therapy, or a radiation therapy. In certain aspects, the second cancer therapy is radiation therapy. Such a therapy may involve, for example, administration of from about 25 to about 65 Gy, from about 35 to about 50 Gy or from about 35 to about 45 Gy of radiation to the patient. Furthermore, in certain cases, the radiation therapy comprises a 3-D conformal planning technique.

As described supra, methods of the invention involve the administration of capecitabine. In certain highly preferred aspects the capecitabine is administered orally. For example, the capecitabine may be administered in a dose of from about 850 to about 1300 $mg/m^2/d$, from about 900 to about 1250 $mg/m^2/d$ or a dose of about 1000 $mg/m^2/d$. Furthermore, in certain cases the dose of celecoxib administered to the patient may be defined as less than about 200 mg b.i.d, more than 200 mg b.i.d or about 200 mg b.i.d. In still further aspects, it may be preferred that the celecoxib and capecitabine are both administered within the same week, the same day, the same hour or essentially simultaneously. Thus, in certain aspects, methods of the invention may involve administering a composition comprising both celecoxib and capecitabin. It will be understood by the skilled artisan that a celecoxib and capecitabine therapy may be administered for any length of time such as 1, 2, 3, 4, 5 or more times over a period of days, weeks, months or years. Thus, in some case, such a therapy maybe administered for two weeks during a three week period.

In still further embodiments the invention concerns pharmaceutical preparations comprising a COX-2 inhibitor and a fluorocytidine derivative. Such a preparation may additionally comprise another anti-cancer agent and may be formulated for use in any of the methods described herein. In preferred embodiments, for example, there is provided a pharmaceutical preparation for formulated oral administration such as one comprising celecoxib and capecitabine.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10A-B: RFS (FIG. 10A) and OS (FIG. 10B) with maintenance versus no maintenance XCEL (study 3).

DESCRIPTION OF ILLUSTRATIVE EMBODIMENTS

Figure 1:
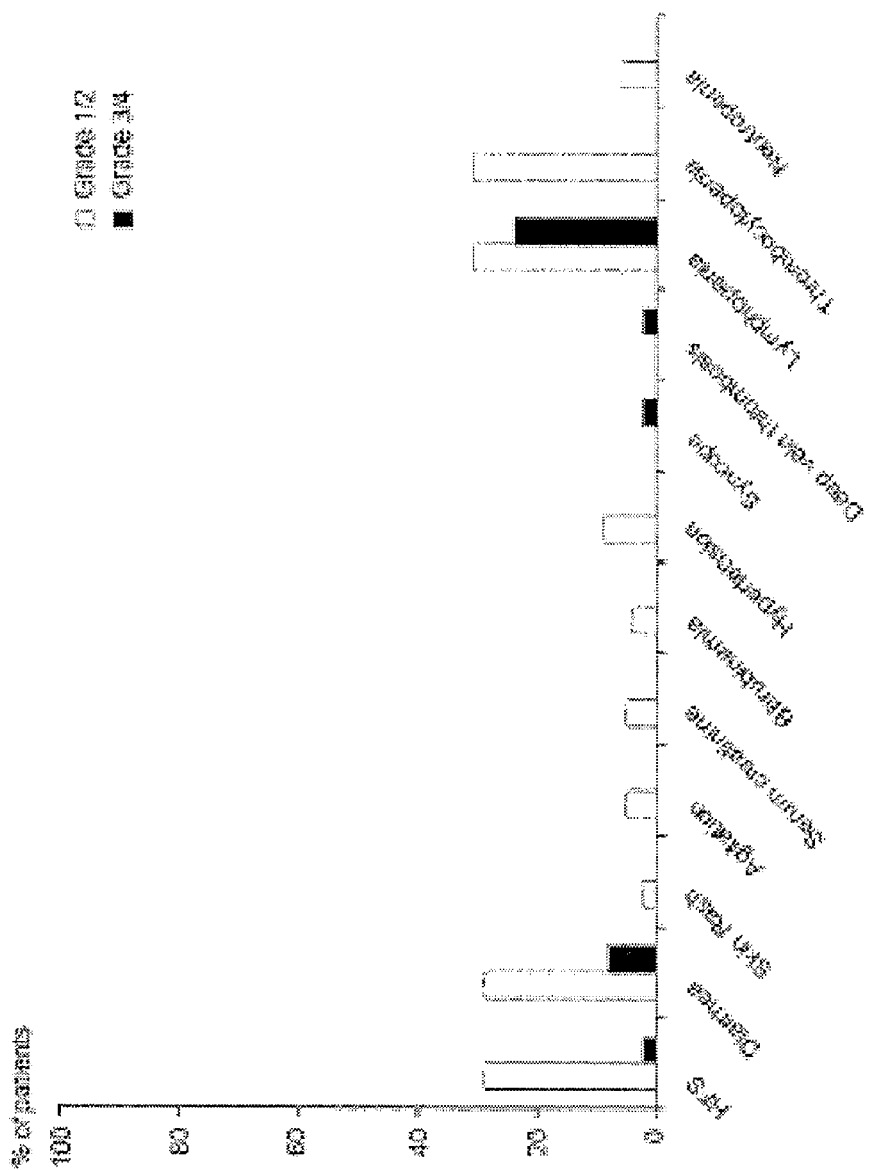
FIG. 1: Common adverse events attributable to XCEL (n=65) (study 1).

The present invention provides, in certain embodiments, methods for the treatment of colorectal cancer comprising administering the celecoxib and capecitabine to a human patient. In certain embodiments, a radiation therapy is also administered to the patient. Other features and advantages of instant invention are detailed below.

I Therapies for Use in Combination with Methods of the Invention

As detailed supra in certain aspects methods of the invention many involve the use of addition anti-cancer therapy. Such addition therapies may be administered to a patient before, after or essentially simultaneously with the treatments of the invention.

Chemotherapy

In certain embodiments of the invention celecoxib and capecitabin are administered in conjunction with other chemo therapeutic agent. For example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, gemcitabien, navelbine, farnesyl-protein tansferase inhibitors, transplatinum, 5-fluorouracil, vincristin, Velcade, vinblastin and methotrexate, or any analog or derivative variant of the foregoing may used in methods according to the invention.

Radiotherapy

In certain preferred embodiments of the invention celecoxib and capecitabin may be used to sensitize cell to radiation therapy. Radio therapy may include, for example, γ-rays, X-rays, and/or the directed delivery of radioisotopes to tumor cells. In certain instances microwaves and/or UV-irradiation may also used according to methods of the invention. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radio therapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B, Her-2/neu, gp240 and p155.

Genes

In yet another embodiment, gene therapy in which a therapeutic polynucleotide is administered before, after, or at the same time as celecoxib and/or capecitabin administration. A variety of genes are encompassed within the invention, for example a gene encoding p53 may be delivered in conjunction with methods of the invention.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. The methods of the present invention may be employed alone or in combination with a cytotoxic therapy as neoadjuvant surgical therapy, such as to reduce tumor size prior to resection, or it may be employed as postadjuvant surgical therapy, such as to sterilize a surgical bed following removal of part or all of a tumor.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other Agents

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

II. Therapeutic Administration

In some embodiments, an effective amount of celecoxib and capecitabin of the invention are administered to a patient. The term "effective amount" as used herein is defined as the amount of celecoxib and/or capecitabin of the present invention that is necessary to result in a physiological change in the patient to which it is administered either when administered alone or in combination with another cytotoxic therapy. The term "therapeutically effective amount" as used herein is defined as the amount of celecoxib and capecitabin that eliminate, decrease, delay, or minimize adverse effects of a disease (e.g., cancer or HFS). A skilled artisan readily recognizes that in many cases methods of the invention may not provide a cure but may only provide partial benefit, such as alleviation or improvement of at least one symptom. In some embodiments, a physiological change having some benefit is also considered therapeutically beneficial. It will additionally be clear that a therapeutically effective amount may be dependent upon the inclusion of additional therapeutic regimens administered concurrently or sequentially. Thus, it will be understood that in certain embodiments a physical change may constitute an enhanced effectiveness of a second therapeutic treatment.

Celecoxib and capecitabin may be administered to a subject per se or in the form of a pharmaceutical composition for the treatment of cancer Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen.

Cancers that may be treated with methods according to the invention include but are not limited to cancers from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some aspects methods of the invention concern systemic formulations include those designed for administration by injection, e.g. subcutaneous, intravenous, intramuscular, intrathecal or intraperitoneal injection, as well as those designed for transdermal, transmucosal, inhalation, oral or pulmonary administration. In the most preferred embodiments celecoxib and capecitabin are delivered by oral administration.

For injection, the proteins of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

Effective Dosages

The celecoxib and capecitabin of the invention will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_5$ as determined in cell culture. Such information can be used to more accurately determine useful doses in humans.

Initial dosages can also be estimated from in vivo data, e.g. animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with IL2-Bax of the invention include, but are not limited to, steroid and non-steroid anti-inflammatory agents.

Toxicity

Preferably, a therapeutically effective dose of celecoxib and/or capecitabin described herein will provide therapeutic benefit without causing substantial toxicity.

Toxicity of the molecules described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975).

Pharmaceutical Preparations

Pharmaceutical compositions of the present invention may comprise an effective amount celecoxib and/or capecitabin (preferably both) and at least one additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least celecoxib or capecitabin or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The compositions of the invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where compositions according to the invention are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

III. Examples

Example 1

Materials and Methods for Study 1

Patients

The institutional review board of The University of Texas M. D. Anderson Cancer Center approved this retrospective expanded cohort study. Between October 2000 and December 2003, seventy-four patients with metastatic colorectal cancer received capecitabine with concurrent celecoxib (n=66), or rofecoxib (n=2), ibuprofen (n=2), sulindac (n=2) and high dose aspirin (n=2). This study analyzed sixty-six patients who received capecitabine and celecoxib (XCEL).

Treatment

Patients who did not receive concurrent radiation therapy received capecitabine orally at a dose of 1000 mg/m2/d twice daily (b.i.d) for 14 days every 21 days, except for four patients who started at 1250 mg/m2/d b.i.d and six elderly patients who started at 900 mg/m2/d b.i.d. All 34 patients who received radiation therapy received capecitabine at 1000 mg/m2/d b.i.d. Monday through Friday during radiation and continued capecitabine at 1000 mg/m2/d b.i.d. for 14 days every 21 days. The radiation was delivered to the target area using 18 MV photons with 3-D conformal planning technique. The dose of radiation was either 35-40 Gy (n=18) or >45 Gy (n=15) with dose radiation missing in one patient. All 66 patients received oral celecoxib continuously 200 mg b.i.d with one of the objectives to mitigate capecitabine induced HFS; while all patients had pain related to tumor (n=37) or musculoskeletal system (n=29). Fifteen patients had required additional opioids. No patients received pyridoxine during this study Responding patients—those who had declining carcinoembryonic antigen (CEA) levels, improved pain control, or stable or decreasing tumor size—continued XCEL until they experienced complete remission, disease progression, or intolerable side effects. All patients experienced pain relief from radiation and/or celecoxib, but formal pain scores were not performed in all patients. Celecoxib was continued with capecitabine to prevent HFS and to improve survival. Six patients had resection of their tumors with curative intent after tumors became respectable after response to XCEL alone or with radiation and four patients had XCEL postoperatively; Two patients had radiofrequency ablations and one patient had palliative resection of colon primary.

Evaluation and Definitions

All patients were subjected to routine clinical examinations, laboratory analyses, and computed tomography. Patients were seen weekly during radiotherapy if treated on site or every 6-9 weeks with physical examinations, laboratory tests, and computed tomography. Treatment-related toxicity was graded using the National Institutes of Health's Common Toxicities Criteria (CTC) version 2.0. Tumor responses were evaluated using RECIST criteria. Complete response was defined as complete radiographic disappearance of measurable or evaluable disease or stable, minimal radiographic findings; partial response was defined as reduction of the longest dimension of measurable disease by at least 50%; stable disease was defined as reduction of the longest dimension by less than 25%; These responses or stable must be confirmed at least by 3 months interval evaluation; Progressive disease was defined as growth of the tumor by more than 25% in the longest dimension or development of new lesions. Overall response rate was defined as the sum of the complete and partial response rates and the tumor control rate was defined as the sum of overall response rates with stable disease rates. The date of death was ascertained through the cancer registry or through a search of patients' social security numbers in the Social Security Death Index (ssdi.genealogy.rootsweb.com). The cutoff point for collection of data was April 2004.

Statistical Analysis

Continuous variables were summarized using the mean (±standard deviation) or the median (range). Comparisons of these variables by patient subgroup (radiation, surgery, high or low lactate dehydrogenase (LDH), and high or low CEA were made using the Wilcoxon rank-sum test. Categorical variables were summarized in frequency tables. Comparisons of important subgroups for these variables were made using the chi-square test or Fisher's exact test, as appropriate. Progression-free survival was defined as the time from the start of XCEL therapy to disease progression or death from any cause. Overall survival was defined as the time from the start of XCEL therapy to death from any cause. Patients were censored at the date of last follow-up if they had not progressed or died. Progression-free and overall survival distributions were summarized using the method of Kaplan and Meier. Differences in progression-free and overall survival by subgroup were analyzed using the log-rank test. Multivariate models of predictors of progression-free survival and overall survival were evaluated using the proportional hazards (Cox) regression model. $P<0.05$ was considered statistically significant.

Example 2

The Effects of Combination Therapy (Study 1)

The patients' baseline clinical and treatment characteristics are summarized in Table 1. The median age of the 24 patients who received first-line XCEL was 73 years (range, 45-86 years), and 7 patients were 78 years or older. Of the 42 patients who received XCEL as second-line therapy, 9 were still responding to the first-line treatment or sensitive to irinotecan-based treatment, the remaining 33 patients' disease had progressed during the first-line treatment. Twenty-four (71%) of the 34 patients who received radiation had prior first-line chemotherapy.

TABLE 1

Baseline Patient, Disease, and Treatment Characteristics (n = 21)

| Category | No. of patients (%) |
|---|---|
| Median age (range) | 64 (30-82 years) |
| <64 years | 11 (52) |
| ≧64 years | 10 (48) |
| Sex | |
| Male | 13 (62) |
| Female | 8 (38) |
| Race | |
| White | 21 (100) |
| Eastern Cooperative Oncology Group (ECOG) performance status | |
| 0 | 12 (68) |
| 1 | 8 (38) |
| 2 | 1 (5) |
| Primary colon cancer | 14 (67) |
| Primary rectal cancer | 7 (33) |

TABLE 1-continued

Baseline Patient, Disease, and Treatment Characteristics (n = 21)

| Category | No. of patients (%) |
|---|---|
| Initial AJCC Stages | |
| II | 4 (19) |
| III | 8 (38) |
| IV | 9 (43) |
| Median disease free interval before metastasis (range) | 6 month (0-72 months) |
| Prior adjuvant 5FU treatment | 8 (45) |
| Median time of last 5-FU treatment to stage IV | 6 months (0-54) |
| Solitary/clustered nodal metastasis | 12 (68) |
| Median Size (range) | 3 cm (2-8.5 cm) |
| Para-aortic and retroperitoneal node†† | 7 (33) |
| Liver† | 2 (9) |
| Pelvis† | 2 (9) |
| Lung | 1 (5) |
| Abdominal wall | 1 (5) |
| None-solitary metastasis | 9 (42) |
| Median size (range) | 3 cm (0.8-15 cm) |
| Median number of metastasis (range) | 4 (2-9) |
| Liver | 4 (19) |
| Liver + lung | 2 (9) |
| Carcinomatosis | 2 (9) |
| Lung | 1 (5) |
| LDH > upper limit of normal | 2 (9) |
| CEA > 3.0 ng/ml (range 3-28) | 8 (38) |
| No radiation | 8 (38) |
| Radiation ≧ 45 Gy | 8 (38) |
| Radiation < 45 Gy | 5 (24) |
| Firstline XCEL | 8 (38) |
| First-line Irinotecan regimens^ | 13 (62) |
| Surgery | 6 (17) |
| Pelvis† | 2 (11) |
| Liver† | 3 (6) |
| Lung | 2 (6) |
| Third-line or fourth line treatment | 3 (17) |

††Three patients had four or more clustered nodal metastases.
†One patient with synchronous rectal tumor and a solitary liver metastasis
^Include 9 patients who responded to first-line Irinotecan with 5-FU, leucovorin or capecitabine.

Toxicities

The median duration of XCEL treatment was 7.2 months (range, 1.5-38 months). Adverse events were available for all but one patient (n=65) summarized in FIG. 1. Most common reason for discontinuing XCEL was progressive disease (n=46). Most common toxicity was lymphopenia of all grades (56%) with 24% being grade ¾ lymphopenia. Incidence of grade 1, 2 and 3 HFS was 14%, 15% and 2% respectively and the median times to HFS onset and peak were 3.8 months (n=17) and 6.0 months (n=12), respectively. Ninety percent of the grade ⅔ HFS occurred after 6 months. Mild serum creatinine elevations (1.6-2.0 mg/dL) occurred in 3 patients after 14 to 32 months of XCEL reversible upon discontinuation of celecoxib. Celecoxib was also discontinued due to grade 2 skin rash (n=1) and grade 2 agitations (n=3). A 56-year-old man experienced two episodes of syncope on cycle 3 and 4 of XCEL presumably because of postural hypotension. No gastrointestinal bleeding, other cardiovascular events, or deaths were noted.

Response Rate

Figure 2:
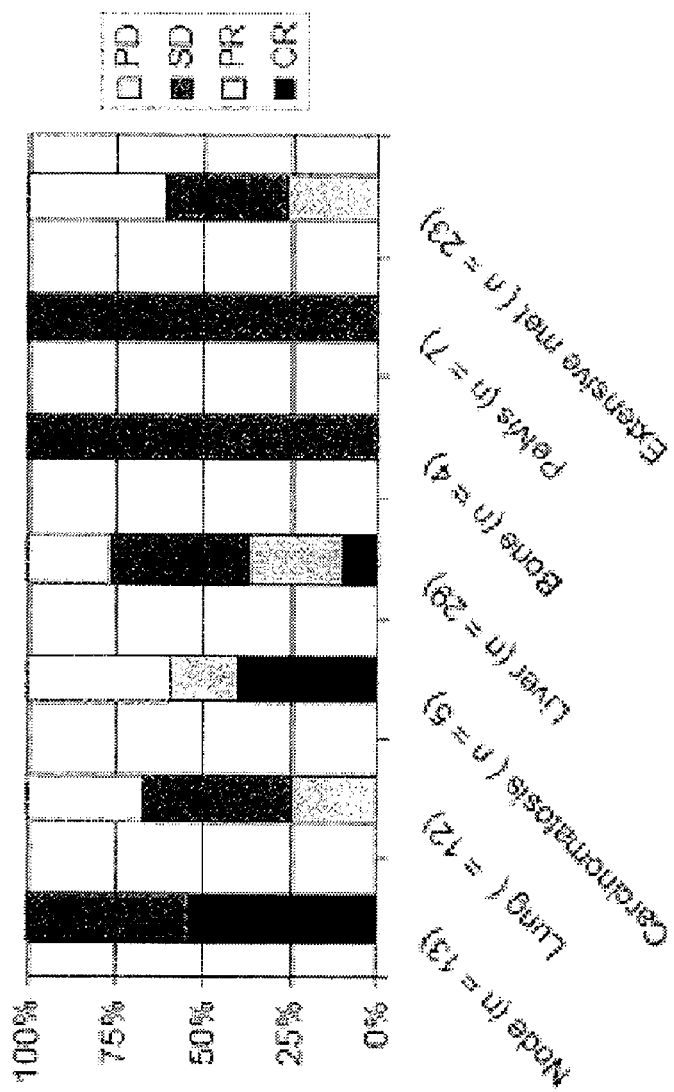
FIG. 2: Response rate by disease sites (study 1).

Of the 66 patients, 13 (20%) achieved a complete response (CR), 12 (18%) achieved a partial response (PR), and 25 (38%) had stable disease (SD), yielding an overall response rate of 38% (95% CI, 26-51%) and a tumor control rate of 76% (95% CI, 60-83%). Of the 24 patients with first-line XCEL, 4 (17%) achieved CR with an overall response rate of 34% (95% CI, 16-55%) and a tumor control rate of 84% (95% CI, 63-95%). Of the 28 patients who had progressed on SFU and irinotecan and received second-line XCEL, 2 (7%) achieved CR, with an overall response rate of 25% (95% CI, 11-45%) and a tumor control rate of 68% (95% CI, 45-80%). The second line overall response rate was 40.5% (95% CI, 27-53%) when all 9 first-line irinotecan responders were included. Complete responses occurred predominantly in patients who received first-line XCEL or after first-line response to irinotecan-based therapy where 7 of 9 patients achieved complete response plus one near complete response (Tables 2 and Table 3). The most common site of complete response was nodal metastasis (51%) followed by peritoneum (40%). No CR was observed for patients with extensive multi-visceral metastasis, but partial responses were seen in all sites except for bone and pelvic metastasis (FIG. 2). Of six patients who had surgery with curative intent, one had pathological CR, 4 had PR and 1 SD from XCEL alone (n=2) or with radiation (n=4).

TABLE 2

Response to XCEL With or Without Radiation

| Tumor response | No. of patients (%) | |
|---|---|---|
| | Radiation (n = 34) | No radiation (n = 32) |
| Complete response | 9 (26) | 4 (13) |
| Partial response | 6 (18) | 6 (19) |
| Overall response | 15 (44) | 10 (31) |
| Stable disease (> 4 months) | 12 (35) | 13 (41) |
| Tumor control | 27 (79) | 23 (72) |

Tumor characteristics, Prior therapies, XCEL duration and Subsequent Therapy (N = 21).

| No. | age/Sex | Tumor site(s) | Size (cm) | No | Initial Rx | RT (Gy) | 1$^{st}$ line RR, Surgery (Margin in mm) | RR XCEL | XCEL Duration | CR duration Months | OS from 1$^{st}$ Rx | OS from XCEL | Subsequent Treatments |
|---|---|---|---|---|---|---|---|---|---|---|---|---|---|
| 1 | 30 M | Liver and rectum | 8.5 | 1 | IFL | 45 | PR, LAR, R Hepatectomy (20 mm) | pCR | 3 mo | 20.5+ | 39+ | 34+ | |
| 2 | 64 F | Para-aortic nodes | 2.6 | 1† | IRI | 50.4 | PR | CR | 22+ | 19+ | 27+ | 22+ | |
| 3 | 75 M | Liver and lung | 0.8 | 5 | XELIRI | — | PR | CR | 12 | 21+ | 28+ | 24+ | |
| 4 | 53 M | Liver | 1.5 | 9 | IFL; XELIRI | — | PR or Near CR | CR | 24 | 28+ | 39+ | 30+ | |
| 5 | 61 F | Mesenteric node | 3 cm | 1 | XELIRI | 45 | PR or Near CR | CR | 5.5 | 27.5+ | 39+ | 30.5+ | |
| 6 | 54 M | Gastrohepatic nodes | 2.2 | 6 | XELIRI | 50.4 | PR | CR | 29 | 14 | 36+ | 27+ | Repeat XCEL radiation, IRI |
| 7 | 67 M | Carcinomatosis | NA | — | XELIRI | — | NA | CR | 3.5 | 13+ | 24+ | 16+ | |
| 8 | 60 M | Aortocaval node | 3.5 | 1 | IFL | 35 | PD | CR | 39+ | 32+ | 59+ | 39+ | Capecitabine alone |
| 9 | 36 F | Para-aortic node | 2.5 | 1† | IFL | 50.4 | PD | CR | 34+ | 36+ | 48+ | 43+ | |
| 10 | 52 F | Liver | 3 | 4 | XELIRI | — | PR | CR | 24+ | 14+ | 30+ | 24+ | |
| 11 | 64 M | Para-aortic node | 2 | 1† | IFL | 35 | PD | SD | 14 | 0 | 51.5+ | 42+ | IFL + Bev, FOLFOX |
| 12 | 49 F | Liver, lung | 3 | 5 | XELIRI | — | PR | PD | 2.5 | 0 | 63+ | 22+ | FOLFOX |
| 13 | 70 M | Inguinal node | 3 | 1 | XCEL | 45 | — | CR | 1.8 | 6 | 36+ | 29+ | None; Alzheimer disease |
| 14 | 64 F | Peritoneal metastasis | 5 | 1 | XCEL | 50.4 | — | CR | 12 | 17 | 26 | 26 | None; patient's choice |
| 15 | 76 M | Retroperitoneal node | 2.6 | 1 | XCEL | — | — | CR | 43+ | 40+ | 46+ | 43+ | |
| 16 | 76 M | Liver | 3 | 1 | XCEL | 50.4 | — | CR | 9 | 10 | 48+ | 35+ | RFA to liver |
| 17 | 62 F | Pelvis | 8 | 1 | XCEL | 39 | SD, APR (Positive margin) | sCR | 6 | 53+ | 57+ | 56+ | |
| 18 | 45 F | Right lung | 2 | 1 | XCEL | — | SD, Wedge (8 mm) | sCR | 16 | 8 | 64 | 39 | IRI, FOLFOX, |
| 19 | 82 M | Lung | 8 | 3 | XCEL | 40 | PR, Wedge (30 mm) | sCR | 4 | 6 | 40 | 38 | XELRI, FOLFOX |
| 20 | 64 M | Liver | 15 | 3 | XCEL | 45 | SD, R Hepatectomy (<1 mm) | sCR | 7 | 8.7 | 47+ | 46+ | FOLFOX, IRI, Erbitox, XCEL |
| 21 | 51 M | Liver | 8 | 2 | IROX | 50.4 | PD R Hepatectomy (1 mm) | sCR | 18 | 13 | 44 | 42 | XCEL, FOLFOX, IRI-Erbitux |

†At least 3-4 clusters nodal metastasis;
XX: first-line responders;
pCR = pathological complete response;
sCR = surgical complete response;
RT = Radiation therapy;
XELIRI = capecitabine + irinotecan;
IFL = 5FU, leucovorin andirinotecan,
CR = complete response.
*History of right hepatic lobectomy
**History of left pneumectomy;
Disease free survival was 8 months after wedge resection

TABLE 3

First-Line or Second-Line XCEL Response With or Without Radiation

| | No. of patients (%) | | | | | |
|---|---|---|---|---|---|---|
| | First-line | | Second-line[a] | | First-line responders[b] | |
| Response rate | Radiation (n = 10) | No radiation (n = 14) | Radiation (n = 20) | No radiation (n = 13) | Radiation (n = 4) | No radiation (n = 5) |
| Complete response | 3 (30) | 1 (7) | 2 (10) | 0 | 3 (75) | 4 (80) |
| Partial response | 1 (20) | 3 (21) | 5 (25) | 2 (15) | 1 (0) | 0 (0) |
| Overall response | 4 (40) | 4 (29) | 7 (35) | 2 (15) | 4 (100) | 4 (80) |
| Stable disease | 4 (40) | 8 (57) | 8 (40) | 5 (38) | 0 (0) | 0 (0) |
| Tumor control | 8 (80) | 12 (86) | 15 (75) | 7 (54) | 4 (100) | 4 (80) |

[a] also including five patients who progressed on first-line irinotecan and oxaliplatin (IROX).
[b] Seven of nine first-line irinotecan responder achieved completer response and one had near complete response.

Survival Analysis

Figure 3:
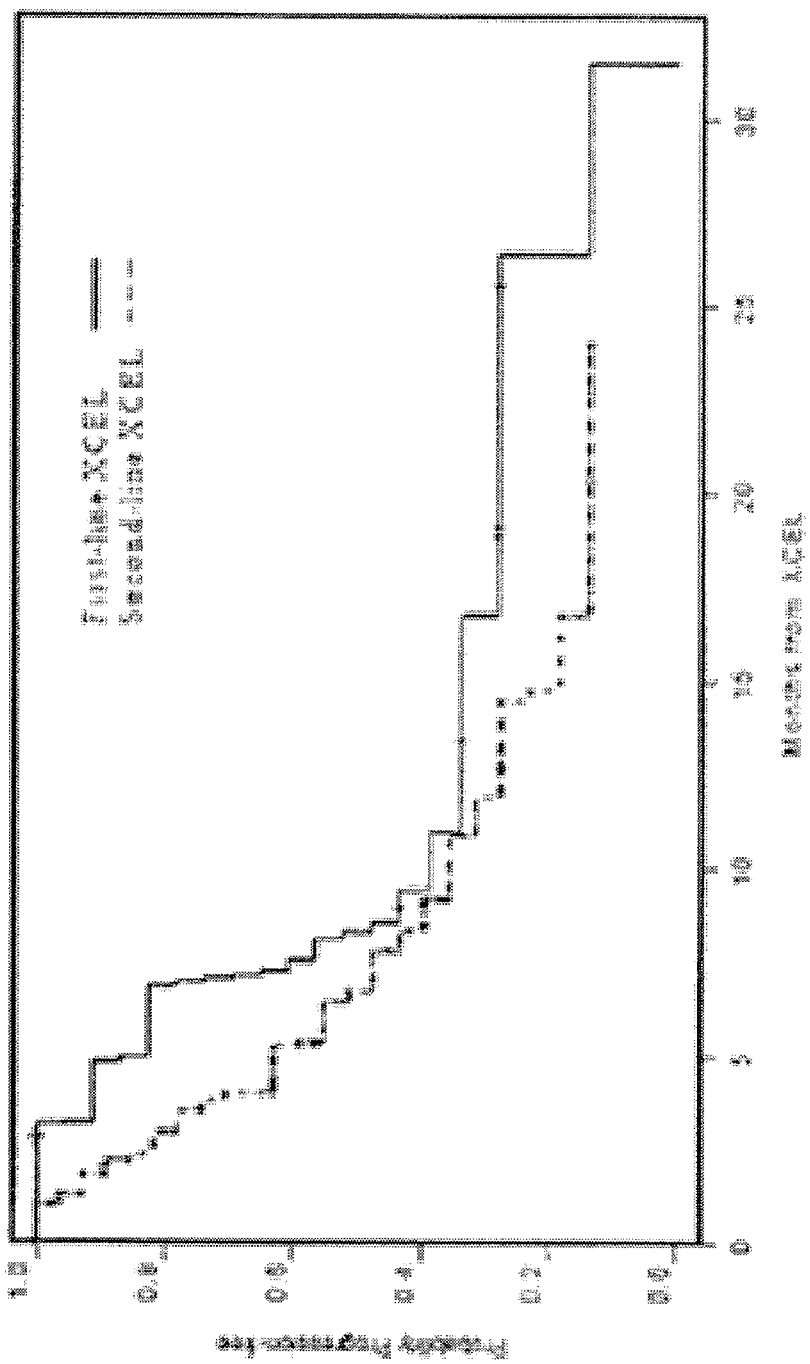
FIG. 3: Kaplan-Meier survival analysis of patients receiving XCEL as first-line or second-line therapy. Graph illustrates progression-free survival (study 1).
Figure 4:
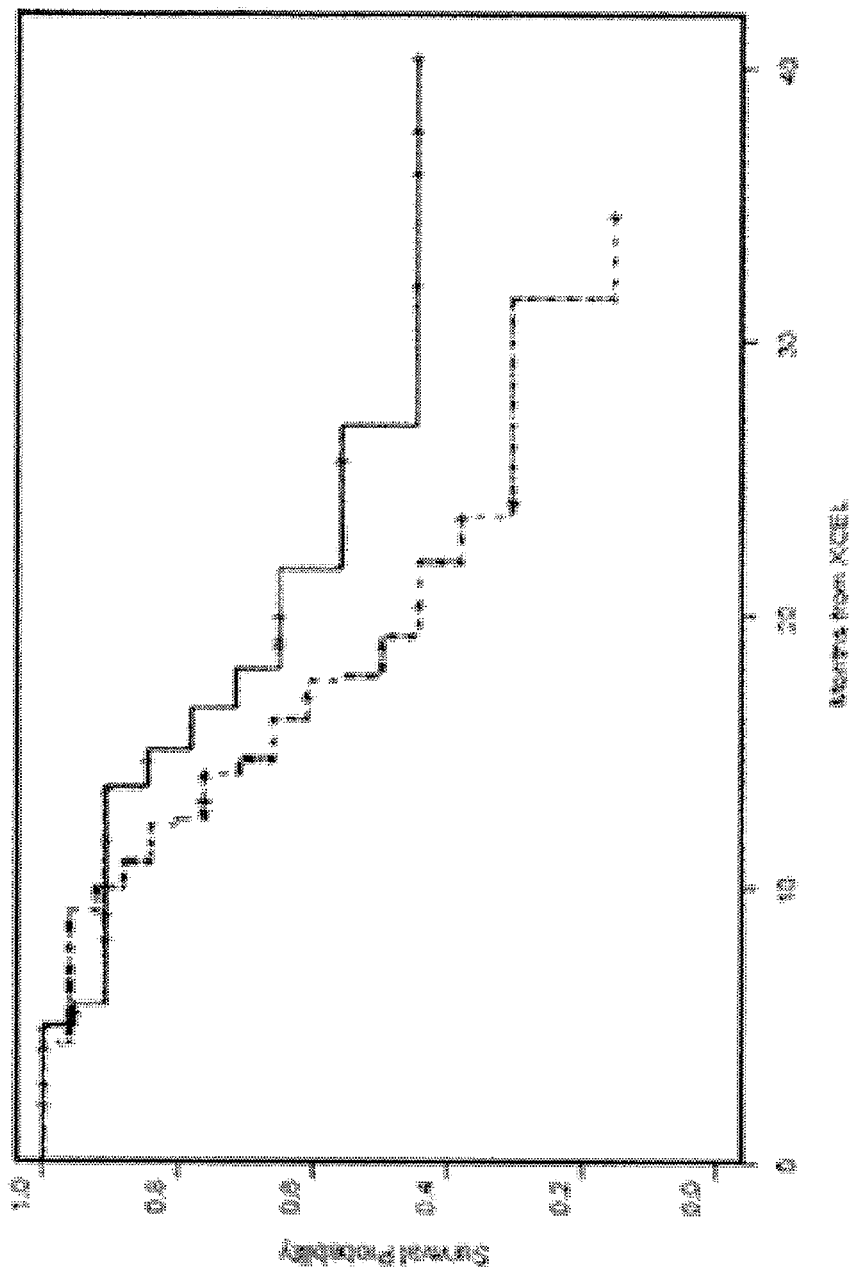
FIG. 4: Kaplan-Meier survival analysis of patients receiving XCEL as first-line or second-line therapy. Graph illustrates overall survival (study 1).

The results of the multivariate analysis of progression-free survival (PFS) and overall survival (OS) are summarized in Table 4. The median PFS was 8.3 months (95% CI, 7.1-16.8 months) for first-line XCEL versus 6.7 months (95% CI, 4.0-11.9 months) for second-line irinotecan refractory group (FIG. 3). The median overall survival was 26.9 months (95% CI 18.0 months-endpoint not reached [NR]) for first-line XCEL versus 17.8 months (95% CI, 14.7-31.5 months) for second-line irinotecan refractory (FIG. 4). The median progression free and median overall survival was 8.3 (5.4-14.5) and 19.3 months (95% CI, 16.2-31.5), respectively when 9 first-line responding patients was included. Median PFS of 21.2 months in patients who received XCEL and radiation (>45 Gy) did not result in prolongation of median OS (P=0.75), but a subset of patients whose median PFS and OS were not reached. Favorable median PFS in patients with normal levels of CEA (P=0.02) and normal levels of LDH (P<0.0001) resulted in improvement of OS for patients with normal LDH (P=0.005); Improvement of OS was also noted in patients who had surgery and radiofrequency ablation (P=0.003).

Discussion

XCEL with radiation resulted in far superior complete response rate, median progression-free survival, and median overall survival compared with historical control with capecitabine monotherapy. These findings also compared favorably to that of combination chemotherapy in first-line and second-line treatment of metastatic colorectal cancer though there are many caveats of making cross-study comparisons (Table 5). The current study findings was limited by its retrospective design and small sample size, and use of radiation that confounded the role of celecoxib in response rate interpretation but not in toxicities; nonetheless, the patients' tumor characteristics were comparable to other studies and median overall survival of 31 months, a finding compatible to that of highly selected surgical series was achieved in 37 patients (56%) who presented with normal level of LDH.29 Furthermore, only 18 patients (28%) of the patients had received all three agents 5-FU, irinotecan, and oxaliplatin, because more than 70% of the patients received XCEL from a period that oxaliplatin was not available in the U.S. The median overall survival was projected to be 14 months based on the Grothey's model that plots percentage of patients who had received 5FU, irinotecan and oxaliplatin to median survival, implicating durable antitumor activity of XCEL (Grothey et al., 2004).

TABLE 4

Time-to-Event Analysis of Patients Receiving XCEL With or Without Radiation*

| | Progression-free survival (months) | | | Overall survival (months) | | |
|---|---|---|---|---|---|---|
| Category | E/N | Median (95% CI) | P value | E/N | Median (95% CI) | P value |
| All | 46/66 | 8.3 (7.0-11.0) | NA | 26/66 | 22.0 (17.8-31.5) | NA |
| No surgery | 39/57 | 7.8 (6.4-9.4) | | 25/57 | 19.3 (16.2-26.9) | |
| Surgery | 7/9 | 16.8 (8.3-31.4) | 0.13 | 1/9 | NR | 0.003 |
| No Radiation (RT) | 25/32 | 7.2 (4.8-9.4) | | 14/32 | 22.0 (16.6-28.8) | |
| RT < 45 Gy | 14/18 | 8.0 (5.4-14.5) | 0.17 | 9/18 | 20.0 (14.7-NR) | 0.75 |
| RT ≧ 45 Gy | 6/15 | 21.2 (7.1-21.2) | | 3/15 | 21.8 (17.6-NR) | |
| CEA ≦ 3.0 ng/ml | 6/17 | 16.8 (9.4-NR) | | 3/17 | 31.5 (18.0-NR) | |
| CEA > 3.0 ng/ml | 35/44 | 7.1 (5.7-9.4) | 0.02 | 23/44 | 20.0 (16.2-26.9) | 0.12 |
| LDH ≦ 618 | 20/37 | 14.5 (9.2-26.3) | | 8/37 | 31.5 (23.6-NR) | |
| LDH > 618 | 26/29 | 6.4 (4.3-7.2) | <0.0001 | 18/29 | 17.6 (14.7-20.0) | 0.005 |

E/N: events/number of patients;
NR: Not reached;
NA: not applicable.
*One patient treated outside the institution did not have radiation dose.

TABLE 5

Cross-study comparison of XCEL to other first-line and second-line therapy

| Category | Capecitabine | XELIR1 | IFL + B[c] | XCEL | FOLFOX = B | Capecitabine[27/28] | XCEL |
|---|---|---|---|---|---|---|---|
| | | First-line therapy | | | | Second-line therapy | |
| Number of patients | 1200 | 52 | 402 | 24 | 290 | 22 | 28 |
| Radiation | No | No | No | Yes | No | No | Yes |
| Refractory to | None | None | None | None | 5-FU, IRI | 5-FU | 5-FU, IRI |
| Complete response (%) | 1 | 0 | 4 | 17 | 0 | 0 | 7 |
| Response rate (%) | 19-25 | 50 | 45 | 33 | 9-20 | 0 | 25 |
| Stable disease (%) | 50 | 21 | NA | 50 | 45-51 | 50 | 50 |
| Median PFS (months) | 4.2 | 7.8 | 10.6 | 8.3 | 4-6 | 2.1 | 6.7 |
| Median OS (months) | 12.4-13.2 | 16.8 | 20.3 | 26.9 | 9.8-12 | 12.7 | 17.6 |

NA: Not available;
B: bevacizumab;
XELIRI: capecitabine and irinotecan; IRI innotecan;
FOLFOX: infusional 5-FU +/− LHOP;
PFS: progression-free survival;
OS: overall survival Radiation is historically reserved as a palliative tool for patients with metastatic colorectal cancer, but was the mainstay of treatment for patients with locally advanced rectal cancer, in whom 20-30% of complete pathological response had been observed with concurrent infusional 5FU or capecitabine (Dawson et al., 2000; Janjan et al., 2000; Lin et al., 2005). Escalated dose of radiation with concurrent hepatic arterial infusion of fluorodeoxyuridine was associated with increased response rate (including complete response) and survival for patients with liver only metastasis (Ben-Josef et al., 2005). Our study and others may herald a trend of moving chemo-radiation beyond the palliative role in the treatment of selected metastatic colorectal cancer patients especially in view of nineteen (29%) complete responses. Detailed clinical and tumor characteristics of complete responses will be discussed in another report. Trimodal treatment capecitabine, celecoxib and radiation in a xenograft pancreas tumor model produced synergistic antitumor effects in both shielded and irradiated tumors, indicating the abscopal effect also observed in the current study (Blanquicett et al., 2005). In contrast, phase II studies combining high dose rofecoxib with bolus 5-FU and leucovorin or combining celecoxib with capecitabine, irinotecan found no added antitumor activity in patients with metastatic colorectal cancer (Becerra et al., 2003; El-Rayes et al., 2005).

Earlier study controlled for capecitabine dose at 1000 mg/m2/d bid indicated that XCEL was associated with lower incidence of grade ⅔ HFS (12.5% versus 34.2%) than capecitabine alone (p=0.037) and reduced grade ¾ diarrhea (Lin et al., 2002). In this expanded study with longer follow up, XCEL resulted in 17% of grade ⅔ HFS, 90% of which occurred after 6 months and median HFS onset and peak occurring at 3.8 months and 6 months respectively. In contrast, patients experienced HFS onset (93%) and most severe episode (67.9%) within six weeks of capecitabine at 1250 mg/m2/d and as high as 17% were grade 3 HFS. Reduced HFS manifestations in the current study could not be simply attributable only to lower dose of capecitabine at 1000 mg/m2/d, as capecitabine starting at 750-1000 mg/m2/d bid with irinotecan also produced 35% HFS (Patt et al., 2004). More importantly, half of the patients on monotherapy capecitabine would have experienced tumor progression (2-4 months) prior to HFS peak of 6 months observed in XCEL study (Van Cutsem et al., 2001; Hoff et al., 2001; Hoff et al., 2004; Lee et at, 2004). Furthermore, lack of HFS time course would also make cross-study comparison of HFS incidences difficult, as celecoxib may not only affect HFS incidence but also may delay its onset and peak (Abushullaih et al., 2002; Hoff et al., 2004; Lee et al., 2004). Nevertheless, this hypothesis is being tested in a National Cancer Institute sponsored prospective, randomized phase III study that compares celecoxib versus placebo on capecitabine-induced HFS in patients with metastatic colorectal and metastatic breast cancers stratified to radiation or no radiation.

Figure 6:
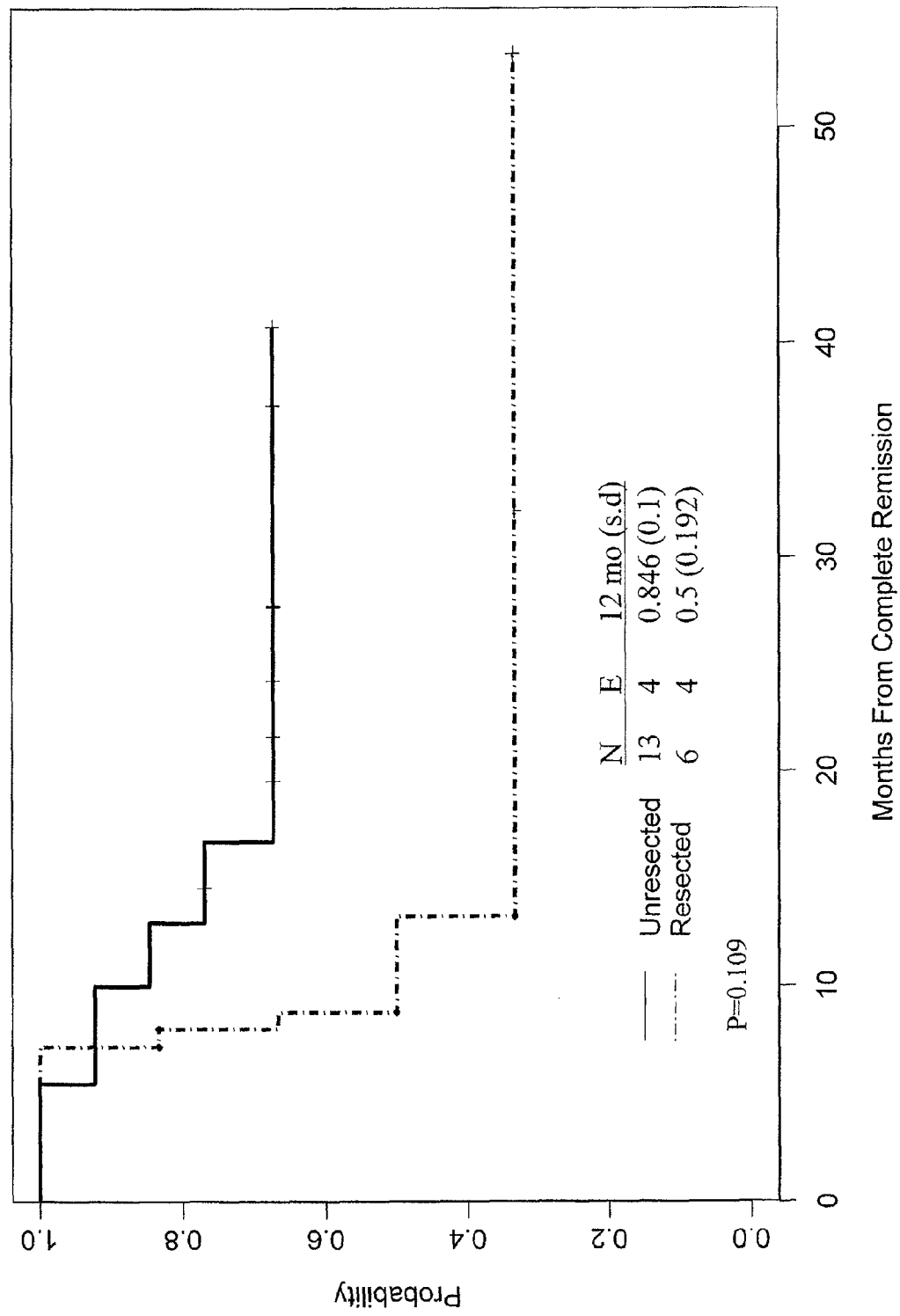
FIG. 6: Complete response duration in resected (n=6) and unresected patients (n=13) (study 2).

Improved clinical outcomes and reduced toxicities with XCEL supported our initial hypothesis that COX-2 activation, a key playmaker of inflammation may be the common mechanism mediating HFS and colorectal cancer progression (FIG. 6). HFS bears all four pathognomic signs of inflammation as well as occasional arthritis flare-up and biopsies of HFS lesions revealed acute inflammatory dermal and vascular injuries (Nagore et al., 2000; Lin et al., 2002). Interestingly, incidence of diarrhea and indirect bilirubinemia, which involves inflammation as well appeared also reduced with XCEL (Lin et al., 2002). Many none-5FU cytotoxic agents e.g. liposomal doxorubicin, cytarabine, vinorelbine, docetaxel as well as cytostatic tyrosine kinase inhibitor of vascular endothelial growth factor receptor (VEGFR) are also known to cause HFS, indicating a common pathophysiological pathway that predisposes hand-foot tissues to these offending agents (Nagore et al., 2000; Escudier et al., 2005; Demetri et al., 2005). Though not studied in the normal hand-foot tissues, COX-2 activation in the tumor in response to chemotherapy and/or radiation was well documented both in experimental models and in patients (Mercer et al., 2005; Altorki et al., 2005). Co-treatment with celecoxib with chemotherapy abrogates the chemotherapy-induced increase in prostaglandin E2 level but not in COX-2 expression in the tumor (Altorki et al., 2005). Besides increased platelet aggregation thanks to unopposed action of thromboxane A2 (Topol, 2005), selective COX-2 inhibitor down regulates VEGF, the ligand of VEGFR and upregulates endostatin and thrombospondin-1, tilting to angiogenic milieu favoring microvascular injuries (Kang et al., 2002; Ma et al., 2002). These antiangiogenic mechanisms explain rapid tumor response, improved survival, and rare reversible renal dysfunction with XCEL (Kang et al., 2002). In contrast, the pathophysiology of HFS would be pro-angiogenic (acute inflammatory) tissue injuries, thus capecitabine induced HFS was reduced with concurrent use of celecoxib. Rare but fatal gastrointestinal and cardiovascular events seen with long-term celecoxib use (Godlstein et al., 2000; Solomon et al., 2005) were fortunately not seen, because current study was small and involved relative short term XCEL that targeted tumor endothelial cells whose turnover rate (2.4-13 days) was 20-2000 times faster than that of normal tissues (47-23,000 days) (Hobson and Denekamp, 1984).

In summary, capecitabine and celecoxib integrating radiation may improve tumor response and survival while may reduce toxicities notably HFS for patient with metastatic colorectal cancer, implicating COX-2 activation as the common mediator. Further understanding of the mechanisms of in vivo COX-2 activation to chemotherapy and/or radiation in normal and tumor tissues may lead to optimal ways of disrupting the COX-2 signaling pathway and improving tumor control through enhanced antiangiogenic strategies including the use of chemo-radiation while preserving the microvascular health particularly in the vital organs.

Example 3

Materials and Methods for Study 2

Patients and Treatment

This retrospective study was approved by the institutional review board of The University of Texas M. D. Anderson Cancer Center. All sixty-six patients received concurrent capecitabine (Xeloda, Roche Nutley, N.J.) at mean daily dose 1000 mg/m²/d bid for 14 days every 21 days or Monday-through Friday with radiation with daily celecoxib (CELEBREX®, Pfizer, NY) at 200 mg PO b.i.d. from October 2000 to December 2003.

Evaluation and Definitions

All patients were subjected to routine clinical examinations, laboratory analyses, and computed tomography before receiving XCEL described previously. All patient data were to be independently audited and radiographic images depicting CR were reviewed and agreed upon by two independent radiologists. All 19 patients had pathological confirmation of metastatic cancer ( ). Treatment-related toxicity was graded using the National Institutes of Health's Common Terminology Criteria for Adverse Events, version 3.0. Tumor responses were evaluated using RECIST criteria with complete response defined as complete radiographic disappearance of measurable or evaluable disease and normalization of tumor marker. The death date was ascertained by searching (ssdi.genealogy.rootsweb.com) using social security numbers. The cutoff point for collection of survival was October 2005.

Statistical Analysis

Continuous variables were summarized using the mean (±standard deviation) or the median (range). Categorical variables were summarized in frequency tables. Comparisons of important subgroups for these variables were made using the chi-square test or Fisher's exact test, as appropriate. Time to complete response was defined as time to start XCEL therapy to first documented radiographic complete response. Duration of complete response was defined as time to first CR to first recurrence or death. Progression free survival was defined as the time from the start of XCEL therapy to disease progression or death from any cause. Overall survival was defined as the time from the start of XCEL therapy to death from any cause. Patients were censored at the date of last follow-up if they had not progressed or died. Progression-free and overall survival distributions were summarized using the method of Kaplan and Meier. All response rates, progression-free survival and overall survival were calculated based on the 95% confidence interval (CI). Event chart was created using symbolized events versus time descriptively.

Example 4

Effects of Combination Therapy (Study 2)

The patients' baseline demographics were summarized in Table 1. All nineteen complete responders were among 21 patients who had solitary/clustered nodal metastasis (n=7) or visceral metastasis (n=5) and/or who had responded to first-line irinotecan (n=9). Unfavorable tumor characteristics were node positive primary (84%), extrahepatic disease (80%), multifocal disease (68%), synchronous primary (33%) and greater than 5 cm tumors (24%). The favorable tumor characteristics were solitary metastasis (42%), normal levels of lactate dehydrogenase (95%) and carcinoma embryonic antigen level <200 ng/ml (95%) and prior response to first-line treatment (43%). However, all patients were unresectable (n=17) or borderline resectable (n=2) including 9 patients with solitary visceral metastasis 3 were found unresectable on surgical explorations, 3 already had prior surgeries, and 3 had significant medical co-morbidities that prohibit surgery (Janjan et al., 2000). The natural history of disease in reference to XCEL treatment and subsequent therapy is summarized by event charts in Table 2 and FIG. 5.

Complete Responses

The median time to CR was 6.5 months (range, 2.5-12.5 months) and the median duration of CR was 13 months for the resected patients, but was not reached for the unresected patients (FIG. 6). All nine patients who had elevated carcinoma embryonic antigen level experienced normalization of CEA (not shown). Of the unresected patients, the most common CR site was nodal disease (43%) followed by liver (36%) and carcinomatosis (21%). Response to XCEL prior to surgery among for the 6 surgical patients was pathological CR (n=1), partial response (n=4) and stable disease (n=1). Eight of nine first-line responders achieved CR except for one nonecompliant patient, who progressed on XCEL despite excellent response to first-line XELIRI. Only one of eight patients with solitary or clustered nodal disease who did not attain CR was a 55 year-old man who was refractory to IFL, then enjoyed stable disease on XCEL plus radiation for 18 months. His disease was stable remained on for 18 months before developing lung and bone metastasis and is currently alive at 51.5 + months since diagnosis.

PFS and OS and Relapse

Figure 5:
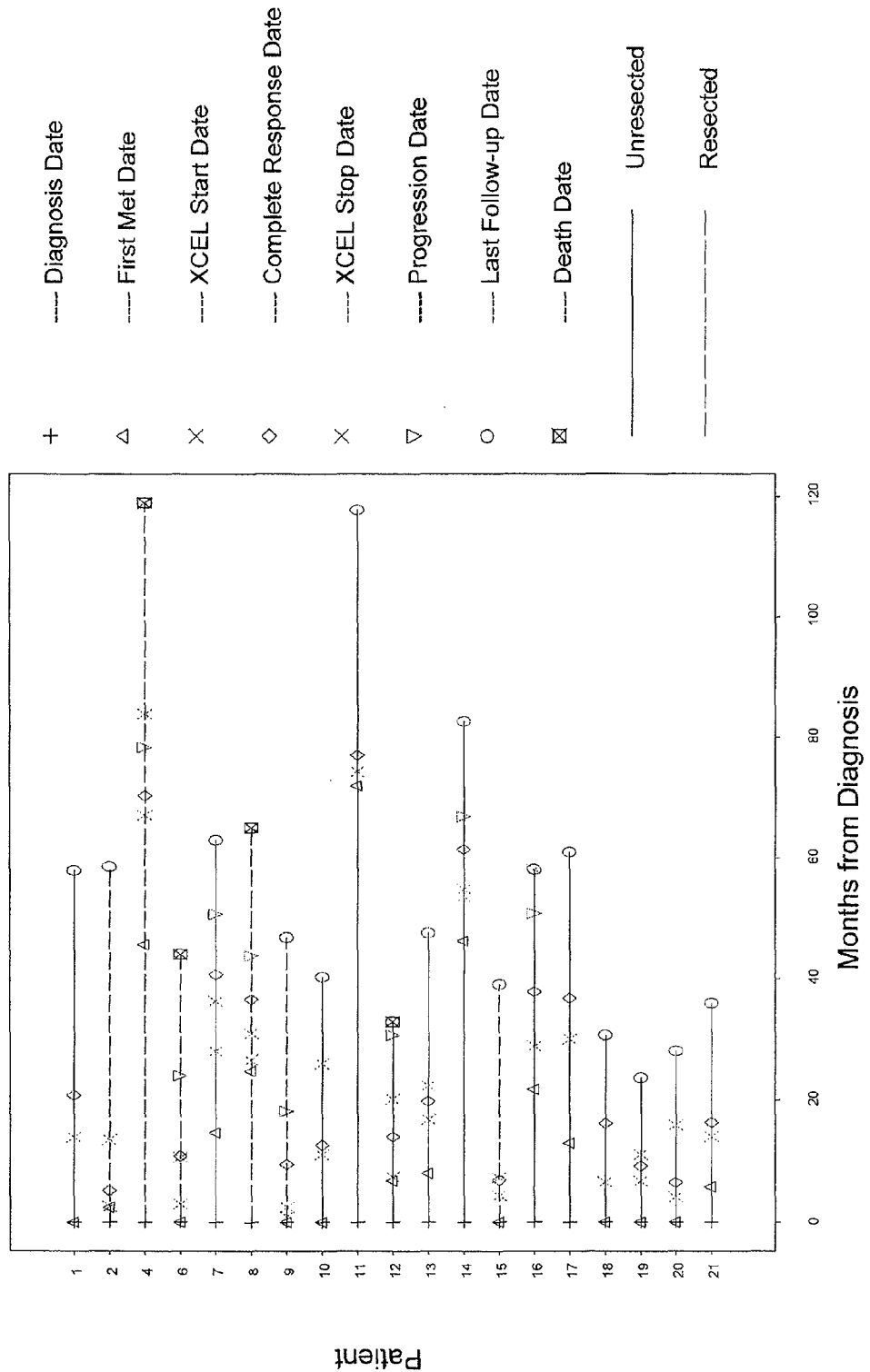
FIG. 5: Event Chart analysis (n=21) (study 2).
Figure 7:
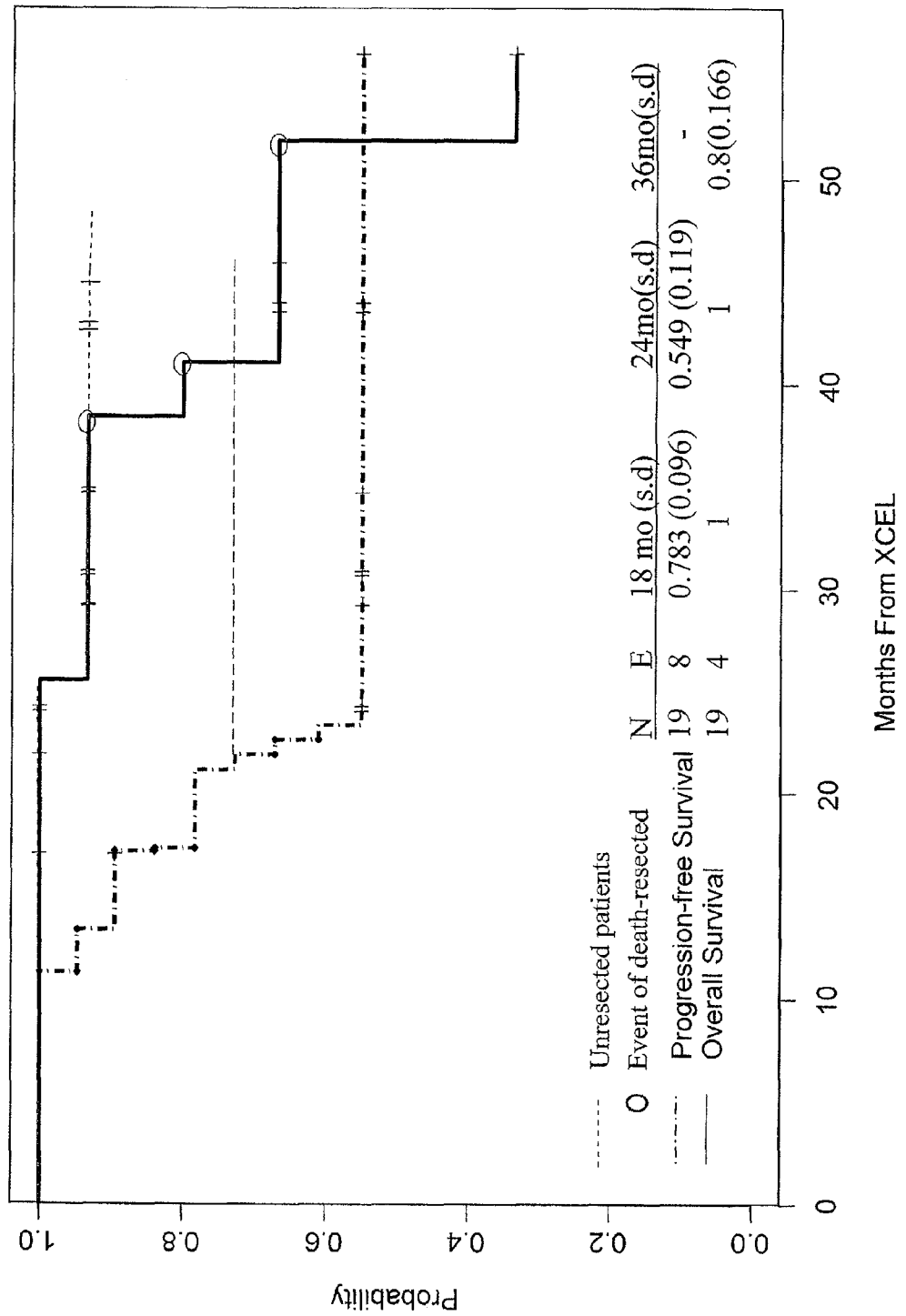
FIG. 7: Progression free survival and overall survival in resected and unresected patients (n=19) (study 2).

Five-year PFS from XCEL was 57% and 71% for all patients and none-surgical group, respectively. Five patients remained on XCEL with longest at 43+ months (FIG. 5). Five-year OS was 64% and 92% for all patients and none-surgical patients respectively (FIG. 7) The median OS was reached at 54 months for all patients because of three deaths in the surgical group. Only one unresected CR patient with solitary peritoneal metastasis died at 24 months since she refused additional therapy after she discontinued after 6 months of XCEL following XCEL plus radiation. The median time to relapse from CR date was 14 months (95% CI, 6-17 months). All eight relapse (41%) occurred at original sites (except for resected patients) equally split between the unresected patients (29%) versus the resected patients (67%) The subsequent treatment was summarized occurring primarily in the resected patients Table 2. The fact that resected patients had bulkier tumors (8-15 cm) and only one CR to XCEL may in part explain the high rate of relapse and death in this group. Interestingly, those patients with positive margin resection have proceeded adjuvant XCEL are still alive as compared to those with positive margins.

Toxicities

Despite the fact that the median duration of XCEL was 12 months (range, 1.8-43 months), the most common reason for discontinuing XCEL was CR from treatment or surgery (n=8) and two discontinued celecoxib for grade 2 agitations and two for late grade 1 elevation in serum creatinine. Similar to the prior report, the most common and one and only grade ¾ toxicity was lymphopenia (28%) of unknown clinical significance. Most common grade ½ toxicity was diarrhea (44%) followed by HFS (28%). Unexplained mild weight gain (n=2) and osteoporosis (n=1) was suspected. Hematologic toxicities were limited to grade 1 neutropenia and thrombocytopenia. Median increases in mean corpuscular volume (MCV) before and after XCEL treatment was 10 (range 5-20) as compared to MCV of –2 in that none-compliant patient.

High rate of sustainable CR was achieved with XCEL integrating multimodality therapy, leading to an unprecedented five year survival in selected colorectal cancer patients with hepatic only as well as extrahepatic metastases despite many unfavorable tumor characteristics. Surprisingly, five-year PFS (70%) and OS (92%) for the unresected CR patients exceeded the historical controls in patients with most favorable resectable liver-only metastasis (Fong et al., 1999; Taieb et al., 2005). Survival for the six resected patients were also favorable since three of six patients had R1 resections (Abdalla et al., 2004). The current study is small and retrospective, but represents a unplanned exhaustive subset of patients, whose prolonged survival was also consistently found for patients who took XCEL in either first-line or second-line settings. The study does not define the role of celecoxib in the survival outcome given that 13 patients (62%) had chemo-radiation and 9 patients (47%) were first-line responders. Until XCEL is validated in prospective study, patients with resectable colorectal cancer metastasis should undergo curative resection when feasible (Fong, 2000; Topham and Adam, 2002; Abdalla et al., 2004; Adam et al., 2001; Kemeny et al., 1999). However, the conventional view that radiation plays only palliative role is challenged by this study especially in those with retroperitoneal nodal metastasis, where the CR rate of 50% was achieved. Progressive disease in these nerve-rich retroperitoneal nodal regions can be detrimental to quality of life.

Following first-line response or chemo-radiation with XCEL or after surgery, XCEL was continued in patients to inhibit the tumor regrowth, leading to CR rate of 90% in first-line responders and sustained CR rate of 70% in the unresected patients. This high rate of CR could have been the sole results of first-line therapy (as there were no CR) and would only be feasible by the sums pathological CR rate (6-30%) and rate of microscopic tumor (20-30%) expected in patients with locally advanced rectal cancer treated with chemoradiation (Lin et al., 2005; Kim et al., 2005). Even though only one patient had confirmed pathological CR (5%) in both liver and in the irradiated rectum, no other CR patient had gone to surgery. Interestingly, six (43%) of 14 patients (including 9 patients with multifocal metastasis) who discontinued XCEL remained in CR at a median follow-up of 36 months, implying the pathological CR rate in this study may be above 5%. In addition, continuation of XCEL after attaining CR in 15 patients would have suppressed the regrowth of microscopic tumor since all relapses occurred following XCEL discontinuation at the initial tumor sites after a median time of 14 months (95% CI, 6-17 months), sufficient for a microscopic tumor to become detectable radiographically at a reported median linear growth rate of 0.083 mm/day (0.008-0.262 mm/day) or median volume doubling time of 130 days (53-1570 days) for colorectal cancer (Bolin et al., 1983).

CR as a result of suppressing microscopic tumor cells from regrowth is reminiscent of tumor dormancy model following prolonged antiangiogenic or metronomic treatment in animal models (O'Reilly et al., 1997; O'Reilly et al., 1996). It lends support to the claim that XCEL may be anti-angiogenic fortuitously followed a metronomic dosing paradigm (Browder et al., 2000; Kerbel and Kamen, 2004). Moreover, one of putative targets of tumor angiogenesis is bone marrow derived circulating endothelial progenitor (CEP), virtually indistinguishable by surface markers from hematopoietic stem cells (HSC) characterized by CD34 and CD133 expression (Lyden et al., 2001; Peichev et al., 2000). Low dose metronomic cyclophosphamide results in normalization of CEP, whereas high dose cyclophosphamide at maximal tolerated dose mobilizes viable CEP consistent with finding in patients with breast cancer patients receiving adjuvant chemotherapy (Bertolini et al., 2003; Furstenberger et al., 2006). Response of combining intermittent cyclophosphamide with metronomic cyclophosphamide produced most durable tumor response than metronomic chemotherapy (Shaked, 2005). CEP levels measured by flow cytometry or by CD133 mRNA are elevated in human cancers and correlated with cancer progression (Mancuso et al., 2003; Lin et al., 2002). Reduction or normalization of CEP levels correlated with response to antiangiogenic therapy (Willett et al., 2004). The inventors suspect that elevated MCV (Sussman et al., 2003), minimal myelosuppresion but profound lymphopenia may be more than a bystander's effect on HSC but a direct or indirect effects on CEP mobilization (Furstenberger et al., 2006). Conversely, the number and function of CEP correlate inversely with cardiovascular risk factors, and independently predict cardiovascular events and death (Hill et al., 2003; Werner et al., 2005), potentially explaining the increased cardiovascular events from anticancer therapies.[4]

In addition to cardiac and renal toxicities concern from celecoxib Lin et al., 2005), the inventors observed unexplained modest weight gain (n=2) and grade 1 osteoporosis (n=1) in patient who took XCEL over 24 months. Even though XCEL was continued beyond 12 months in 70% of the patients, the overall toxicities profiles were favorable. Continuing maintenance XCEL beyond CR may result in overtreating 10-30% of patients on chemoradiation or 1-5% of the patients on chemotherapy, assuming these patients may have achieved complete pathological CR in both gross and microscopic tumors. Since XCEL is orally self-administered, one patient later admitted none-compliance, whose peak MCV increase before and after XCEL was –2 compared to a mean +10 in the compliant patients. Serial MCV may be used as a surrogate of capecitabine compliance (Sussman et al., 2003).

In summary, XCEL resulted in unprecedented sustained CR rate, PFS and OS in selected patients with metastatic colorectal cancer, converting a sub-acute disease to a chronic one. The fact that XCEL is all-oral, safe, and inexpensive, and may be broadly applicable to all first-line responders may have far reaching implications since the newer first-line chemotherapies with targeted agents are expensive and did not improve CR rate despite improved response rate up to 80% Hurwitz et at, 2004; Diaz Rubio et al., YR; Hochster, 2006). CR was also feasible with XCEL in patients who responded to first-line oxaliplatin combination. Studies with metronomic chemotherapy with or without selective COX-2 inhibitor so far had reported very modest antitumor activity because only patients who were heavily pretreated, or refractory to treatment were included without integration of radiation therapy (Werner et al., 2005; Shaked et al., 2005; Kieran et al., 2005; Spieth et al., 2003). Beyond the ongoing randomized phase III study to discern the effects of celecoxib on capecitabine induced hand-foot syndrome, the inventors intend to molecularly classify these CR patients beyond the clinical characteristics and to better understand mechanism of CR in relationship to tumor dormancy, and to optimize the dose and schedule duration of XCEL using CEP and other markers as a surrogate marker.

Example 5

Materials and Methods for Study 3

Patients

The institutional review board approved this study. All nineteen patients with unresectable metastatic colorectal cancer started XCEL (capecitabine 1000 mg/m2/day BID and celecoxib 200 mg PO BID) from February 2001 to November 2003. Eleven patients had first-line irinotecan with either 5FU or capecitabine and 8 patients took XCEL+radiation as first-line therapy. Six patients had negative margin (R0) or microscopic margin (R1) resections, one of which was pathological CR and two had gross positive margin (R2) resections prior to XCEL. All patients had clinical examinations, laboratory and CT scan every 2-3 months. Maintenance XCEL (extended adjuvant therapy) is defined as continuation of XCEL beyond radiologic or surgical CR (n=14).

Evaluation and Definitions

The principal investigator and two board-certified radiologists reviewed all the CT scan images. CR was defined according to the RECIST criteria as complete disappearance of measurable or none-measurable disease. Effective CR (eCR) was coined to describe normalization of an anatomical structure (e.g. nodes) that cannot regress completely. Confirmed CR included those patients who had CR by meeting the RECIST criteria or had achieved eCR or pathological CR. Near CR (nCR) were defined as almost complete disappearance (95-99%) of measurable disease on CT scan. Relapse free survival (RFS) was defined as the time from first radiologic CR to first recurrence, progression, or death. Progression free survival (PFS) time was defined as the time from the start of XCEL to recurrence, progression of measurable disease or death form any cause. OS was defined as the time from first radiologic CR to death from any cause. Treatment related toxicity was graded in accordance with the National Cancer Institute Common Toxicity Criteria for Adverse Events, version 3.0.

Statistical Analysis

Continuous variables were summarized using the median (range) and categorical variables were summarized in frequency tables. Patients were censored at the date of last follow-up if their disease had not progressed or if they had not died. The death date was ascertained by searching (ssdi.genealogy.rootsweb.com) using social security numbers or phone follow-up. Therefore, it was possible for censored OS times to be greater than censored RFS and PFS times. Kaplan-Meier estimates for RFS, PFS, and OS were calculated, and group comparisons made using log-rank tests. The analyzed prognostic and treatment factors include: maintenance therapy (yes or no), resections (unresected/R1-2 or R0), site (intrahepatic or extrahepatic), tumor size (>8 cm or less), metastasis number (single versus multifocal), initial stage on diagnosis (stage II or stage III/IV), disease free interval prior to stage IV disease (6 months or less), LDH prior to XCEL (normal versus abnormal), radiation (yes or no), and response to first-line irinotecan based treatment (yes or no).

Example 6

Effects of Combination Therapy Study 3

Patient Characteristics

Figure 9:
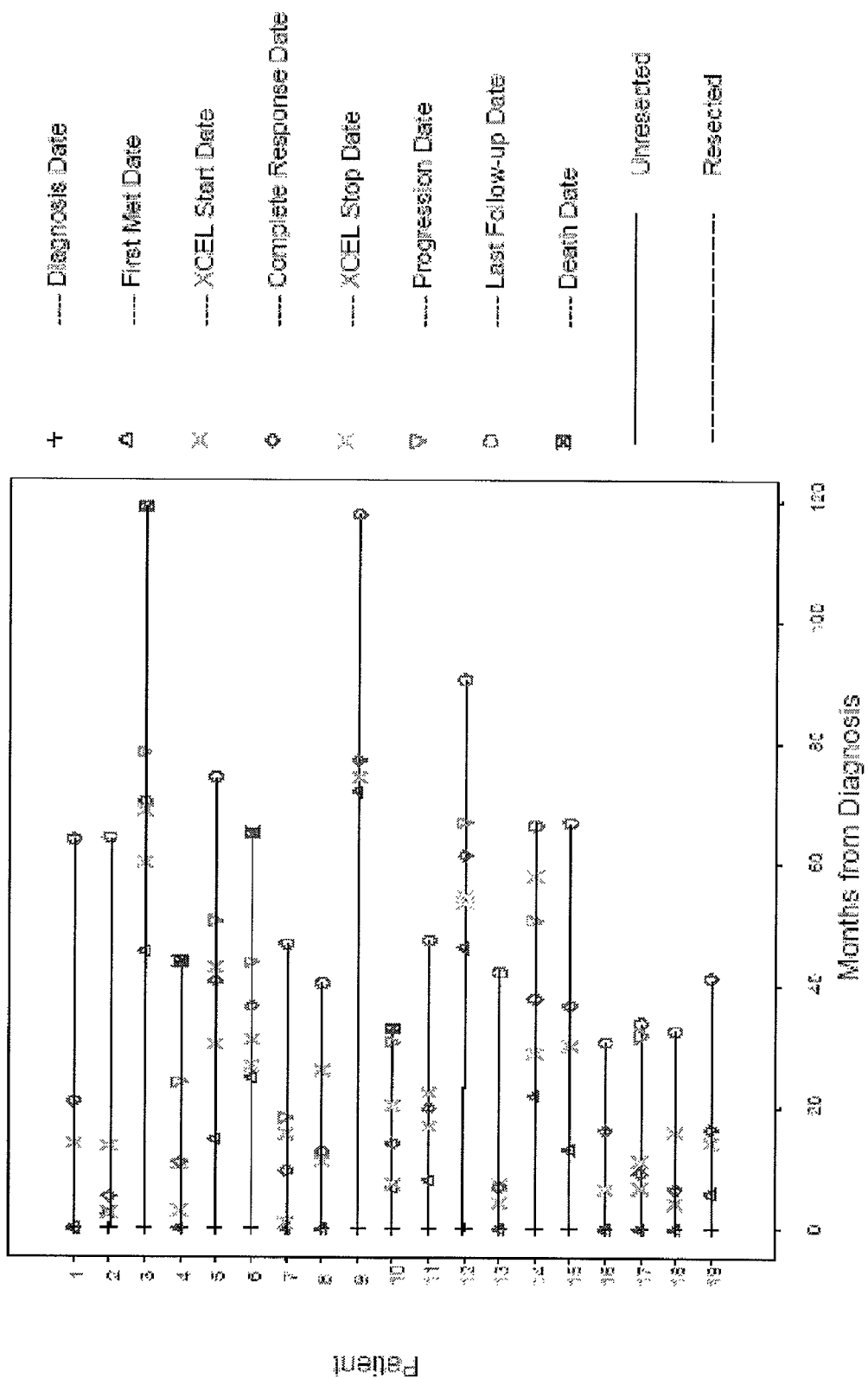
FIG. 9: Event chart analysis from diagnosis of colorectal cancer (study 3).

Patient demographics are summarized in Table 6. Detailed treatment and survival characteristics are shown in Table 7 and FIG. 9. All patients had either pathologic confirmation of metastasis (n=15) or elevated tumor marker and unequivocal radiographic evidence of metastasis (n=4). Poor prognostic factors included node positive primary or stage IV disease on presentation (16/19, 84%), extrahepatic disease (13/19, 68%), or multifocal disease (10/19, 53%), or tumor size >8 cm (5/16, 31%), resistance to first-line irinotecan based treatment (3/19, 16%). The favorable prognostic characteristics were normal levels of lactate dehydrogenase (16/19, 84%), carcinoma embryonic antigen level <200 ng/ml (18/19, 95%), responses to first-line therapy (11/19, 58%) and solitary metastasis (9/19, 47%). The median disease free interval before metastasis was 5.7 months (95% CI 3.9-23.5 months). Following downsizing with neoadjuvant chemotherapy with XCEL+radiation, five had R0 resections of the metastatic disease and one had a R1 resection and two had R2 resections prior to initiating therapy. The pathological findings were: one pathological CR, two microscopic residue disease, and five macroscopic disease. Twelve patients had radiotherapy (35-50.4 Gy) with XCEL and eight were responding to first-line irinotecan regimens.

TABLE 6

Baseline Patient, Disease, and Treatment Characteristics (n = 19)

| Category | No. of patients (%) |
| --- | --- |
| Median age (range) | 62 (30-82 years) |
| Sex | |
| Male | 13 (68) |
| Female | 6 (32) |
| Race | |
| White | 19 (100) |
| Eastern Cooperative Oncology Group (ECOG) performance status | |
| 0 | 10 (53) |
| 1 | 8 (42) |
| 2 | 1 (5) |
| Primary colon cancer | 12 (64) |
| Primary rectal cancer | 7 (36) |
| Initial AJCC Stages | |
| II | 3 (16) |
| III | 7 (37) |
| IV | 9 (47) |
| Median time to stage IV disease(months) | 5.9 (0-73) |
| Median size (centimeter n = 16) | 3 (0.8-15) |
| Solitary metastasis | 9 (47) |
| Noda[†] | 3 (16) |
| Liver[††] | 2 (11) |
| Peritoneum | 2 (11) |
| Lung | 1 (5) |
| Pelvis | 1 (5) |
| None-solitary metastasis | 10 (53) |
| Median number of metastasis (range) | 4 (2-9) |

TABLE 6-continued

Baseline Patient, Disease, and Treatment Characteristics (n = 19)

| Category | No. of patients (%) |
|---|---|
| Liver | 4 (22) |
| Liver + lung | 2 (11) |
| Carcinomatosis | 2 (11) |
| Lung | 1 (5) |
| Elevated CEA > 3.0 ng/ml (range 3-2250) | 10 (53) |
| Elevated CA19.9 | 1 (5) |
| Radiation | |
| ≥45 Gy | 9 (47) |
| <45 Gy | 3 (16) |
| None | 7 (37) |
| Firstline XCEL | 8 (42) |
| First-line Irinotecan | 11 (58) |
| Post-XCEL R0-I resections | 6 (32) |
| Pelvis | 2 (11) |
| Liver†† | 3 (6) |
| Lung | 2 (6) |

†Three patients had clustered nodal metastases.
††One patient with synchronous rectal primary and liver metastasis

TABLE 7

Summary of the tumor characteristics and survival from XCEL and pattern of relapse.

| No. | Age/Sex | Tumor site(s) | Size (cm) | Tumor Number | First-line Treatment | RT (Gy) | Independent review [resections R0-2] |
|---|---|---|---|---|---|---|---|
| 1 | 60 M | Aortocaval node | 3.5 | 1 | IFL | 35 | eCR |
| 2 | 62 F | Palvis | 8 | 1 | XCEL | 39 | SD (R1) |
| 3 | 45 F | Right lung | 2 | 1 | XCEL | — | SD (R0) |
| 4 | 51 M | Liver | 8 | 2 | IROX | 50.4 | PR (R0) |
| 5 | 76 M | Liver | 3 | 1 | XCEL | 50.4 | nCR |
| 6 | 82 M | Lung | 8 | 3 | XCEL | 40 | PR (R0) |
| 7 | 54 M | Liver | 15 | 3 | XCEL | 45 | PR (R0) |
| 8 | 53 M | Liver | 1.5 | 9 | IFL/XELIRI | — | CR |
| 9 | 76 M | Small bowel | NA | 1 | XCEL | — | Unconfirmed [R2] |
| 10 | 64 F | Poritoneal metastasis | 5 | 1 | XCEL | 50.4 | Unconfirmed |
| 11 | 61 F | Mesenteric node | 3 | 1 | XELIRI | 45 | CR |
| 12 | 70 M | Inguinal node | 3 | 1 | XCEL | 45 | Unconfirmed |
| 13 | 30 M | Liver and recium | 8.5 | 1 | IFL | 45 | pCR(R0) |
| 14 | 54 M | Gastrochepatic nodes | 2.2 | >6 | XELIRI | 50.4 | nCR |
| 15 | 36 F | Para-aortic node | 2.5 | 4 | IFL | 50.4 | eCR |
| 16 | 52 F | Liver | 3 | 4 | XELIRI | — | CR |
| 17 | 67 M | Carcinomatasis | NA | >2 | XELIRI | — | Unconfirmed [R2] |
| 18 | 75 M | Liver and lung | 0.8 | 5 | XELIRI | — | CR |
| 19 | 64 F | Para-aortic node | 2.6 | 1* | IRI | 50.4 | eCR |

| No. | Maintenance XCEL | RFS from CR months | CS from met | Relapse/Death | Subsequent Treatments |
|---|---|---|---|---|---|
| 1 | yes | 43.2 | 63.5 | No | |
| 2 | yes | 54.2 | 63.0 | No | |
| 3 | no | 20.3 | 73.4 | Yes/Yes | IRL FOLFOX |
| 4 | no | 13.4 | 44.0 | Yes/Yes | XCEL, Al six agents |
| 5 | yes | 10.1 | 59.6 | Yes/No | RFA to liver |
| 6 | no | 7.3 | 40.2 | Yes/Yes | XELRI, FOLFOX |
| 7 | yes | 8.9 | 45.0 | Yes/No | All six agents, XCEL + RT |
| 8 | yes | 40.1 | 40.1 | No | |
| 9 | yes | 41.4 | 52.7 | No | |
| 10 | yes | 17.0 | 33.0 | Yes/Yes | None: patient's choice |
| 11 | yes | 28.1 | 47.3 | No | Lose for CT soan but not survival |
| 12 | no | 5.6 | 47.3 | Yes/No | RFA to inguinal node |
| 13 | yes | 38.0 | 44.3 | No | |
| 14 | yes | 13.1 | 42.5 | Yes/No | XCEL + RT, IRI only |
| 15 | yes | 31.6 | 54.9 | No | |
| 16 | yes | 18.7 | 34.6 | No | |
| 17 | yes | 27.9 | 36.3 | Yes/No | |
| 18 | yes | 27.0 | 33.1 | No | |
| 19 | yes | 25.1 | 35.3 | No | |

*At least 3-4 clusters nodal metastasis,
pCR = pathological complete response;
eCR = effective CR;
uCR = near CR;
PR = Partial response;
SD = stable disease.
PD = progressive disease.
NA = not available.
RT = Radiation therapy;
XELIRI = capecitabine and innotecan Complete Response All nineteen patients had at least one report indicating no radiographic evidence of disease agreed by one of two independent radiological reviews. The second independent review was also able to verify the radiological findings in all but 4 of 19 patients. The confirmed CR patients included 1 pathologic CR patient, 3 eCR, 4 CR and 7 surgically resected patients (4 R0 resections, 1 R1 resection and 2 R2 resections). Interestingly, the pathological CR occurred in a patient with a solitary liver metastasis that did not completely regress radiographically. Four unconfirmed CR patients were only evident retrospectively with two patients whose respective inguinal node or peritoneal mass could not be distinguished from post radiation changes; and in two near CR patients. One near CR patient was found to have a residue 1.2 cm gastro-hepatic node among diffuse abdominal nodes (>3 cm) regressed to sub-centimeter nodes following chemoradiation. The other near CR patient had solitary liver metastasis had regressed from 3 cm to 2 mm following radiotherapy plus XCEL (Table 7). All patients with elevated serum carcinoma embryonic antigen (CEA) or elevated CA19.9 levels had their CEA or CA19.9 normalized during CR.

RFS

Nine patients relapsed during the follow-up at 5 to 27 months following CR. Two-year RFS was 57% (Table 8). The median RFS was not reached (95% Confidence Interval [CI], 17 months—[NR] not reached) Paradoxically, two-year RFS was 71% (95% CI, 0.51-1.00) for the 14 unresected and R1-2 resected patients versus 20% (95% CI, 0.03-1.00) for the five R0 resected patients, one of whom was a pathologic CR patient (p=0.07), or versus 0% excluding the one pathological CR patient (p=0.015). Two-year RFS estimate was 73% (95% CI, 0.54 to 1.00) for the maintenance XCEL group versus 0% without maintenance XCEL (p=0.002) (FIG. 10A.). Other prognostic and treatment factors did not predict RFS (Table 8). Consistent with the other report, all relapses occurred exclusively in situ except for the resected patients following discontinuing or not initiating maintenance XCEL after CR. Among nine relapses, five were retreated with XCEL alone or with radiation, two had radiofrequency ablation, and one had resection at the anastomosis site indicating the nature of in situ relapses. A sensitivity analysis calculated the log-rank tests reported in Table 8 using a dataset excluding the 4 patients with unconfirmed CR. The results were similar for predicting both RFS and OS, with an exaggeration of the RFS (p=0.0005) advantage for not achieving R0 resections. A paradoxical PFS advantage in the unresected and R1-2 resected patients (p=0.069) and in patients who received maintenance XCEL (p=0.002) was also observed.

TABLE 8

Time to event analysis for relapse free survival (RFS) and overall survival (OS), n = 19.

| | | E/N | 2-year RFS (95% CI) | P-value* | E/N | 3-year OS (95% CI) | P-value* |
|---|---|---|---|---|---|---|---|
| All patients | | 9/19 | 0.57 (0.39, 0.85) | | 4/19 | 0.79 (0.59, 1.00) | |
| Maintenance XCEL | yes | 5/15 | 0.73 (0.54, 1.00) | .002 | 1/15 | 0.93 (0.82, 1.00) | .04 |
| | no | 4/4 | 0.00 | | 3/4 | 0.38 (0.08, 1.00) | |
| Metastectomy | none/R1-2 | 5/14 | 0.71 (0.51, 0.99) | .07 | 1/14 | 0.93 (0.80, 1.00) | .13 |
| | R0 | 4/5 | 0.20 (0.03, 1.00) | | 3/5 | 0.60 (0.29, 1.00) | |
| Extrahepatic | yes | 6/13 | 0.50 (.20, 1.00) | .12 | 3/13 | 0.67 (0.33, 1.00) | .60 |
| | no | 3/6 | 0.52 (0.15, 1.00) | | 1/6 | 0.79 (0.66, 1.00) | |
| Tumor size | <8 cm | 4/11 | 0.62 (0.39, 1.00) | .35 | 1/11 | 1.00 | .46 |
| | ≧8 cm | 3/5 | 0.40 (0.14, 1.00) | | 2/5 | 0.60 (0.29, 1.00) | |
| Metastatic Number | solitary | 4/9 | 0.56 (0.31, 1.00) | .71 | 2/9 | 0.89 (0.71, 1.00) | .42 |
| | non-solitary | 5/10 | 0.60 (0.36, 1.00) | | 2/10 | 0.60 (0.29, 1.00) | |
| Stage at Diagnosis | II/III | 6/10 | 0.40 (0.19, 0.85) | .22 | 3/10 | 0.77 (0.53, 1.00) | .30 |
| | IV | 3/9 | 0.78 (0.55, 1.00) | | 1/9 | 0.83 (0.58, 1.00) | |
| Disease-free interval prior | <6 mo | 3/10 | 0.64 (0.44, 1.00) | .10 | 1/10 | 0.75 (0.54, 1.00) | .19 |
| To metastasis | ≧6 mo | 6/9 | 0.50 (0.38, 1.00) | | 3/9 | 0.74 (0.39, 1.00) | |
| LDH | Abnormal | 3/3 | 0.33 (0.07, 1.00) | .08 | 1/3 | 0.50 (0.13, 1.00) | .45 |
| | Normal | 6/16 | 0.62 (0.42, 0.91) | | 3/16 | 0.85 (0.68, 1.00) | |
| Radiation | yes | 6/12 | 0.50 (0.28, 0.88) | .68 | 2/12 | 0.79 (0.56, 1.00) | .58 |
| | no | 3/7 | 0.69 (0.40, 1.00) | | 2/7 | 0.75 (0.43, 1.00) | |
| Response to first-line therapy | yes | 3/9 | 0.58 (0.39, 1.00) | .28 | 0/9 | 1.00 | .15 |
| | no | 6/10 | 0.40 (0.25, 1.00) | | 4/10 | 0.65 (0.49, 1.00) | |

E = number of events in category;
N = number of patients in category;
CI = confidence interval * log-rank test

OS

Four patients died during follow-up including 3 R0 resected patients who did not receive any maintenance therapy and 1 unconfirmed CR patient who elected no further therapy after eight months of maintenance XCEL. The estimated 3-year survival rate from CR and from diagnosis was 79% (95% CI, 0.59-1.00) and 95% (95% CI, 0.85-1.00) respectively. The median OS from XCEL and from onset of metastasis reached 51.9 months (95% CI, 45 months—not reached [NR]) and 73.3 months (95% CI, NR-NR months) respectively. Improved OS was associated with maintenance XCEL (p=0.04) (FIG. 10B), reaching a four year OS of 93% from CR but not with any other prognostic or treatment factors (Table 8).

Toxicities

Figure 8:
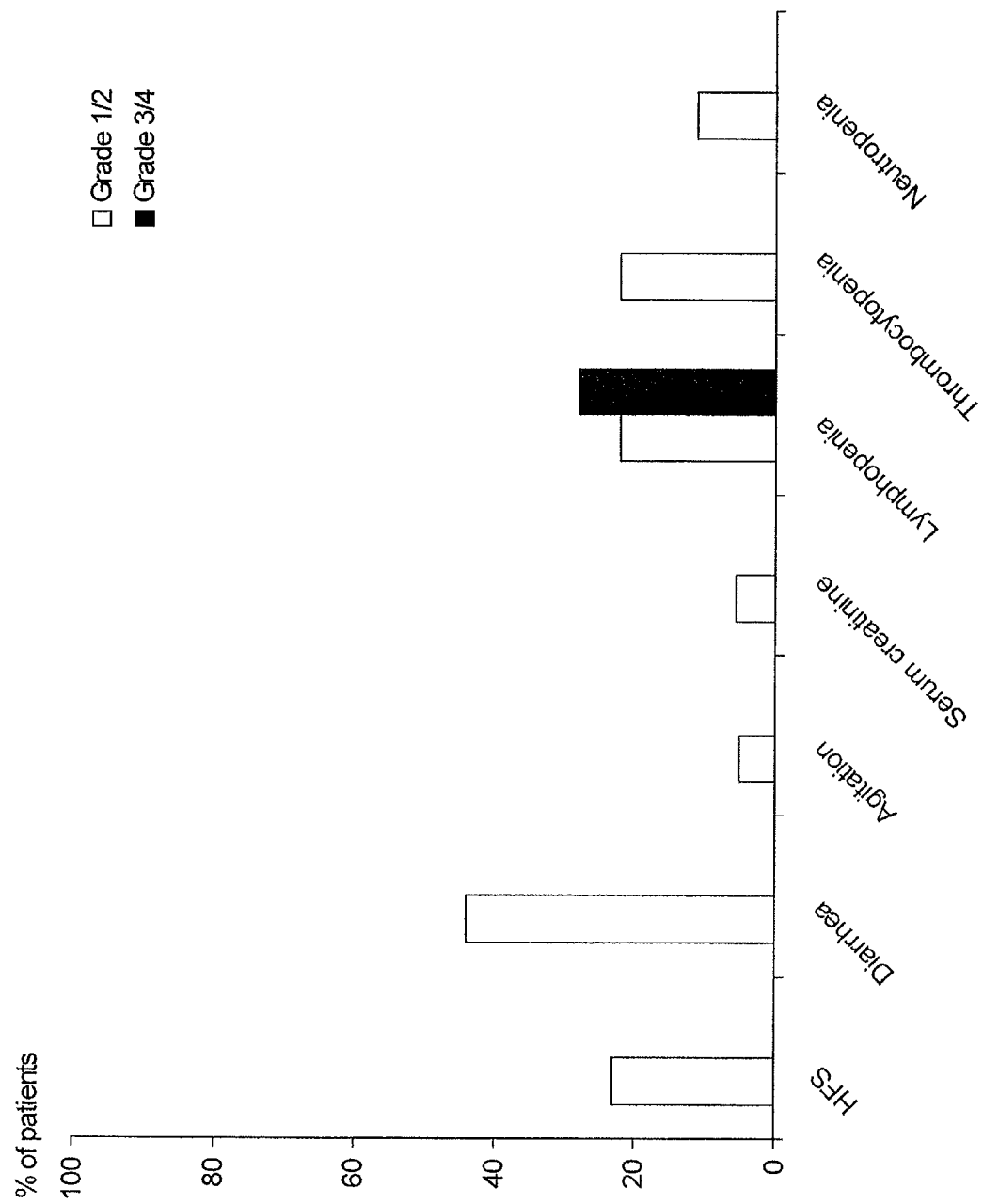
FIG. 8: Attributable adverse events (study 2).

The toxicities were very similar to the previous report (results identical to FIG. 8). 18 One patient discontinued celecoxib after two years of XCEL due to a grade 1 elevated serum creatinine. Median mean corpuscular volume (MCV) increase from baseline after XCEL was 11.5 (95% CI, 8-14). No cardiovascular toxicities were encountered in this group and all patients who had received XCEL for 12 months or more also received 81 mg aspirin daily.

Discussion

Maintenance XCEL, but not any other measured prognostic or treatment factors conferred survival advantage. One may attribute this effect due to a difference in CR, as confirmed CR patients enjoyed a 3-year PFS of 100% versus 0% with unconfirmed CR patients versus 37% for the R0-2 resected patients. Interestingly, five of eight non-surgical CR patients continued maintenance XCEL beyond 24 months (range 27-50.3 months), in contrast, unconfirmed CR patients either did not receive or had less than 6 months of maintenance XCEL. The observations were incidental and the analysis was based on exclusively all "CR" patients from the XCEL database from October 2000 through November 2003. The magnitude of survival even with the selection bias was nonetheless provocative and the RFS and OS among R0-1 resected patients were consistent with the historical controls. Even though this study includes only 19 patients, a statistical significant difference in RFS and OS emerged for those patients who took maintenance XCEL by univariate log rank analysis.

Maintenance XCEL is hypothesized to target colorectal cancer micrometastases, as no patient relapsed while on XCEL. All 9 relapses occurred in situ, except for the four R0 resected cases, consistent with other reports that majority (84%) of CR patients relapsed in situ within the first year. The median time from CR to relapse in the current study was 13.1 months, a time sufficient for micrometastases to become radiographically detectable at a median linear growth rate of 0.083 mm/day (range 0.008-0.262 mm/day) reported for colorectal cancer. Among the resected patients following neoadjuvant XCEL plus radiation, we found one had a pathological CR and two had microscopic residue disease, these findings reminiscent of the patients with LARC treated with chemoradiation. Occasionally, microscopic disease or pathological CR was also seen in patients with metastatic colorectal cancer responding to combination chemotherapy. Eight of nine first-line irinotecan responders had achieved CR (88%) with XCEL alone or with radiation, a rate achievable only by combining the rate of microscopic residue disease and rate of pathological CR. The pathological CR rate is not known, but may be higher than the observed 5% (1/19), as 14 patients did not have resections and the 3 year RFS had reach 57% for the whole cohorts. Expanded clinical experience suggests that maintenance XCEL following CR appeared be reproducible with other first line combination chemotherapy. Effectively targeting colorectal cancer micrometastases with maintenance XCEL led to durable clinical CR, a finding similar to the tumor dormancy models, in which tumor xenografts would regress to a dormant.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,966,891
Abdalla et al., *Ann. Surg.*, 239:818-825, 2004.
Abushullaih et al., *Cancer Invest.*, 20:3-10, 2002.
Adam et al., *Ann. Surg. Oncol.*, 8:347-353, 2001.
Altorki et al., *Clin. Cancer Res.*, 11:4191-4197, 2005.
Becerra et al., *Int. J. Cancer*, 105:868-872, 2003.
Ben-Josef et al., *J. Clin. Oncol.*, 23:8739-8747, 2005.
Bertolini et al., *Cancer Res.*, 63:4342-4346, 2003.
Blanquicett et al., *Clin. Cancer Res.*, 11:8773-8781, 2005.
Bolin et al., *Ann. Surg.*, 198:151-158, 1983.
Borner et al., *Eur. J. Cancer*, 38:349-358, 2002.
Browder et al., *Cancer Res.*, 60:1878-1886, 2000.
Cassidy et al., *J. Clin. Oncol.*, 22:2084-2091, 2004.
Cianchi et al., *Gastroenterology*, 121:1339-1347, 2001.
Cunningham et al., *N. Engl. J. Med.*, 351:337-345, 2004.
Dawson et al., *J. Clin. Oncol.*, 18:2210-2218, 2000.
Demetri et al., *Proc. Am. Soc. Clin. Oncol.*, 23:308, 2005.
Diaz Rubio et al., *Proc. Am. Soc. Clin. Oncol.*, 23(16s)3535, 2005.
Douillard et al., *Lancet.*, 355:1041-1047, 2000.
El-Rayes et al., *Proc. Am. Soc. Clin. Oncol.*, 23(308):3677, 2005.
Escudier et al., *Proc. Am. Soc. Clin. Oncol.*, 23(380):4510, 2005.
Fabian et al., *Invest. New Drugs*, 8:57-63, 1990.
Fong et al., *Ann. Surg.*, 230:309-318, 1999.
Fong, *Adv. Surg.*, 34:351-381, 2000. Furstenberger et al., *Br. J. Cancer*, 94(4):524-531, 2006.
Giantonio et al., *Proc. Am. Soc. Clin. Oncol.*, 23(16s):2, 2005.
Goldberg et al., *J. Clin. Oncol.*, 22:23-30, 2004.
Goldstein et al., *Am. J. Gastro.*, 95:1681-169, 2000.
Grothey et al., *J. Clin. Oncol.*, 22:1209-1214, 2004.
Hill et al., N. Engl. J. Med., 348:593-600, 2003.
Hobson and Denekamp, *Br. J. Cancer*, 49:405-413, 1984.
Hochster, *Semin. Oncol.*, 33:S8-14, 2006
Hoff et al., *J. Clin. Oncol.*, 9:2282-2292, 2001.
Hoff et al., *J. Clin. Oncol.* 22:2078-2083, 2004.
Howe and Dannenberg, *Semin., Oncol.*, 29:111-119, 2002.
Hurwitz et al., *N. Engl. J. Med.*, 350:2335-2342, 2004.
Janjan et al., *Int. J. Radiation Biol. Phys.*, 47:713-718, 2000.
Jemal et al., *CA Cancer J. Clin.*, 55:10-30, 2005.
Kang et al., *J. Am. Soc. Nephrol.*, 13:806-816, 2002.
Kemeny et al., *N. Engl. J. Med.*, 341:2039-2048,1999.
Kerbel and Kamen, *Nat. Rev. Cancer*, 6:423-436, 2004.
Kieran et al., *J. Pediatr. Hematol. Oncol.*, 27:573-581, 2005.
Kim et al., *Int. J. Radiat. Oncol. Biol. Phys.*, 63(2):346-353, 2005.
Lee et al., *Jpn. J. Clin. Oncol.*, 34:400-404, 2004.
Lin et al., *Oncology*, 16s:31-37, 2002,
Lin et al., *Proc. Am. Soc. Clin. Oncol*, 23:269, 2005.
Lin et al., *AACR*, Abstract # 1342, 2002.
Lyden et al., *Nat. Med.*, 7(11):1194-1201, 2001.
Ma et al., *Proc. Natl. Acad. Sci. USA*, 99:13243-13247, 2002.
Mancuso et al., *Pathophysiol. Haemost. Thromb.*, 33:503-506, 2003.
Masferrer et al., *Cancer Res.*, 60:1306-1311, 2000.
Mercer et al., *Anticancer Drugs*, 16:495-500, 2005.
Nagore et al., *Am. J. Clin. Dermatol.*, 1:225-234, 2000.
O'Reilly et al., *Cell*, 88:277-285, 1997.
O'Reilly et al., *Nat. Med.*, 2:689-692, 1996.
Patt et al., *Proc. Am. Soc. Clin. Oncol.*, 22(15s):3602, 2004.
Peichev et al., *Blood*, 95:952-958, 2000.
Remington's Pharmaceutical Sciences, 18th Ed. Mack Printing Company, pp. 1289-1329, 1990.
Rothenberg et al., *J. Clin. Oncol.*, 21:2059-2069, 2003.
Shaked et al., *Cancer Res.*, 65:7045-7051, 2005.
Shaked et al., *Blood*, 106:3058-3061, 2005.
Sheehan et al., *JAMA*, 282:1254-1257, 1999.
Sheng et al., *Cancer Res.*, 58:362-366, 1998.

Solomon et al., *N. Engl. J. Med.*, 352:1071-1080, 2005.
Spieth et al., *Cancer Chemother. Pharmacol.*, 52:377-382, 2003.
Sussman et al., *Cancer Biol. Therapy*, 2:255-256, 2003.
Taieb et al., *J. Clin. Oncol.*, 23:502-509, 2005.
Topham and Adam, *Semin. Oncol.*, 29:3-10, 2002.
Topol, *JAMA*, 293:366-368, 2005.
Tournigand et al., *J. Clin. Oncol.*, 22:229-237, 2004.
Meta-Analysis Group In Cancer, *J. Clin. Oncol.*, 16:3537-3541, 1998.
Van Cutsem et al., *J. Clin. Oncol.*, 19:4097-4106, 2001.
Werner et al., *N. Engl. J. Med.*, 353:999-1007,2005.
Willett et al., *Nat. Med.*, 10: 145-147, 2004.

The invention claimed is:

1. A method for treating cancer in a human patient comprising administering an effective amount of celecoxib and capecitabine to the patient, wherein the cancer is a nodal metastasis of a metastatic colorectal cancer.

2. The method of claim 1, wherein the nodal metastasis is a solitary nodal metastasis.

3. The method of claim 1, wherein the nodal metastasis is a clustered nodal metastasis.

4. The method of claim 1, wherein the patient has not been previously treated for the cancer.

5. The method of claim 1, wherein the patient has been previously treated for the cancer.

6. The method of claim 5, wherein the previous treatment comprised administration of irinotecan to the patient.

7. The method of claim 5, wherein the previous treatment comprised administration of surgery to the patient.

8. The method of claim 1, wherein the method further comprises administration of a second cancer therapy to the patient.

9. The method of claim 8, wherein the second cancer therapy is a chemotherapeutic, an anti-cancer drug, a surgical therapy, or a radiation therapy.

10. The method of claim 9, wherein the second cancer therapy is a radiation therapy.

11. The method of claim 10, wherein the radiation therapy comprises administration of from about 25 to about 65 Gy of radiation to the patient.

12. The method of claim 11, wherein the radiation therapy comprises administration of from about 35 to about 50 Gy of radiation to the patient.

13. The method of claim 12, wherein the radiation therapy comprises administration of from about 35 to about 45 Gy of radiation to the patient.

14. The method of claim 13, wherein the radiation therapy comprises a 3-D conformal planning technique.

15. The method of claim 1, wherein the method reduces the probability of capecitabine-induced hand-foot syndrome in the patient.

16. The method of claim 1, wherein the fluorocytidine derivative is administered orally.

17. The method of claim 16, wherein the fluorocytidine derivative is administered at a dose of from about 850 to about 1300 mg/m$^2$/d.

18. The method of claim 16, wherein the fluorocytidine derivative is administered at a dose of from about 900 to about 1250 mg/m$^2$/d.

19. The method of claim 16, wherein the fluorocytidine derivative is administered at a dose of about 1000 mg/m$^2$/d.

20. The method of claim 1, wherein the COX-2 inhibitor is administered at a dose of about 200 mg b.i.d.

* * * * *